(12) United States Patent
Aebersold et al.

(10) Patent No.: US 8,501,421 B2
(45) Date of Patent: Aug. 6, 2013

(54) METHOD FOR HIGH THROUGHPUT PEPTIDE/PROTEIN ASSAY GENERATION AND ASSAYS GENERATED THEREWITH

(75) Inventors: Rudolf Aebersold, Zurich (CH); Paola Picotti, Zurich (CH); Oliver Rinner, Zurich (CH); Johan Malmstroem, Lund (SE)

(73) Assignee: Eidgenossische Technische Hochschule Zurich, Zurich (CH)

( * ) Notice: Subject to any disclaimer, the term of this patent is extended or adjusted under 35 U.S.C. 154(b) by 362 days.

(21) Appl. No.: 12/994,093

(22) PCT Filed: May 20, 2009

(86) PCT No.: PCT/EP2009/003611
§ 371 (c)(1),
(2), (4) Date: Nov. 22, 2010

(87) PCT Pub. No.: WO2009/141141
PCT Pub. Date: Nov. 26, 2009

(65) Prior Publication Data
US 2011/0178273 A1 Jul. 21, 2011

(30) Foreign Application Priority Data
May 23, 2008 (EP) .................... 08009454

(51) Int. Cl.
*G01N 31/00* (2006.01)
*G01N 33/53* (2006.01)

(52) U.S. Cl.
USPC ........... 435/7.21; 435/7.1; 436/501; 436/518; 422/50; 422/430; 530/300; 530/350

(58) Field of Classification Search
None
See application file for complete search history.

(56) References Cited

U.S. PATENT DOCUMENTS
2005/0003450 A1   1/2005   Rush et al.

FOREIGN PATENT DOCUMENTS
| EP | 1 734 367 A1 | 12/2006 |
| EP | 1 988 103 A2 | 11/2008 |
| WO | 2005-124341 A2 | 12/2005 |
| WO | 2006/026569 A2 | 3/2006 |

OTHER PUBLICATIONS

Vinzenz Lange, et al., "Targeted Quantitative Analysis of *Streptococcus pyogenes* Virulence Factors by Multiple Reaction Monitoring," Molecular & Cellular Proteomics 7.8, XP009107637, pp. 1489-1500, 2008.
Viveka Mayya, et al., "Absolute Quantification of Multisite Phosphorylation by Selective Reaction Monitoring Mass Spectrometry," Molecular & Cellular Proteomics 5.6, XP-002501278, 2006, pp. 1146-1157.
Leigh Anderson, et al., "Quantitative Mass Spectrometric Multiple Reaction Monitoring Assays for Major Plasma Proteins," Molecular & Cellular Proteomics 5.4, XP-002438814, 2006, pp. 573-588.
Bernd Bodenmiller, et al., "ProsphoPep-a phosphoproteome resource for systems biology in *Drosophila* Kc167 cells," Molecular Systems Biology, 2007, pp. 1-11.
Kermit K. Murray, et al., "Standard Definitions of Terms Relating to Mass Spectrometry, (IUPAC Recommendations 2006), " IUPAC, Aug. 31, 2006, pp. 1-48.
Eric W. Deutsch, et al., "Human Plasma PeptideAtlas," Proteomics, 2005, pp. 3497-3500, vol. 5.
Parag Mallick, et al., "Computational prediction of proteotypic peptides for quantitative proteomics," Nature Biotechnology, Letters, Jan. 2007, pp. 125-131, vol. 25, No. 1.
Bruno Domon, et al., "Mass Spectrometry and Protein Analysis," Science, Tools for Biochemistry, Apr. 14, 2006, pp. 212-217, vol. 312.
Kai Hilpert, "Peptide arrays on cellulose support: SPOT synthesis, a time and cost efficient method for synthesis of large numbers of peptides in a parallel and addressable fashion," Nature Protocols, 2007, pp. 1333-1349, vol. 2, No. 6.

*Primary Examiner* — Lisa Cook
(74) *Attorney, Agent, or Firm* — Sughrue Mion, PLLC

(57) ABSTRACT

The invention relates to a method for the determination of an MRM or SRM assay for a protein of interest, a peptide of interest, or a group of proteins/peptides of interest or a whole proteome. It essentially includes the following steps: (1) a list of proteins of interest is selected and for each member at least one or a list of candidate proteotypic peptides is derived (2) this at least one peptide is synthesized/generated essentially without subsequent purification; (3) this at least one unpurified peptide is analyzed by selected reaction monitoring (SRM) preferably coupled to liquid chromatography (LC-SRM) or analogous techniques; (4) validation and/or optimisation of the corresponding assay of the at least one peptide with determination of the SRM coordinates for a peptide/protein of interest and/or of a regulator of interest is achieved. A protein sample of interest is enzymatically digested and can then be analyzed in SRM mode or time-constrained SRM mode, using elution times to trigger acquisition of the set of selected SRM traces, thus drastically increasing the throughput. The analysis allows to detect and quantify the set of peptides/proteins of interest. The method additionally relates to a tagging strategy to achieve absolute quantification of the peptides/proteins of interest at low-budget and high-throughput.

29 Claims, 5 Drawing Sheets

METHOD FOR HIGH THROUGHPUT PEPTIDE/PROTEIN ASSAY GENERATION AND ASSAYS GENERATED THEREWITH

TECHNICAL FIELD

The present invention relates to the field of the determination of SRM/MRM assays for the detection and/or quantification of peptides resulting from a protein sample of interest, such as for example of a group of proteins, an organelle or a whole proteome. The present invention furthermore relates to the use of such assays for the analysis of proteomes, for example for the comparison of wild-type and mutant or regulated proteome digests.

BACKGROUND OF THE INVENTION

Biology as a whole and proteomics in particular are moving towards the accurate quantification of large numbers of analytes in the context of specific experiments. In the case of proteomics, the analytes are typically peptides generated by tryptic digestion of protein samples. Systems biology experiments require accurate quantification of the same set of analytes over multiple samples, typically representing cells in differentially perturbed states. This stringent requirement derives from the long term goal of systems biology projects to generate mathematical models that simulate the system studied and make specific predictions about its behaviour under different conditions. While the comprehensive quantitative analysis of the transcriptome became readily accessible with the advent of the micro-array and other transcript profiling technologies, quantitative proteomic analyses to a similar depth and consistency are not achievable by the current proteomic approaches that are based on the generation of fragment ions from precursor ions selected automatically based on the precursor ion profiles (data dependent analysis, DDA). Besides their limited sensitivity, a main shortcoming of these methods is poor reproducibility of target selection which results in only partially overlapping protein sets if substantially similar samples are analyzed repeatedly. Such fragmentary data is also unsatisfactory for multiple applications beyond systems biology, e.g. biomarker discovery, in which complete quantification profiles for each element of a protein set in multiple samples are required. Therefore, new approaches are required which deliver precise quantitative data from defined sets of proteins reliably from multiple samples.

While gene expression analysis is a very mature technology, quantitative proteomics thus still suffers substantial technical limitations. The currently most used proteomics approaches are non-targeted, i.e. in each measurement they quasi-randomly sample a fraction of the proteome. Each repeat analysis required for comparing a proteome at different states, will sample only a subset of a set of proteins of interest, and not necessarily the same subset in each repeat, thus precluding the generation of complete datasets e.g. as when they are required for modelling biological systems. An additional limitation to a comprehensive proteomic analysis is the difficulty in detecting low abundant proteins. These limitations strongly affect the possibility to quantitatively measure key target proteins across different samples, e.g. in the context of biomedical, pharmacological or biological applications. Additionally they precluded so far the coverage of a whole proteome, in spite of the considerable efforts worldwide to identify complete proteomes.

Systems biology relies on data sets in which the same set of proteins is consistently identified and accurately quantified in multiple samples, a requirement that current shotgun approaches can therefore only partially meet. Selected/Multiple Reaction Monitoring (SRM/SRM) mass spectrometry is emerging as technology that ideally complements the discovery capabilities of shotgun proteomics by its unique potential for reliable and comprehensive quantification of substances of low abundance in complex samples.

Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z>fragment m/z (e.g. 673.5>534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. Although broadly used, the term multiple reaction monitoring to indicate the parallel acquisition of multiple SRM transitions might be in the future deprecated by the IUPAC nomenclature. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity.

In this application the terms SRM and MRM or also SRM/MRM can be used interchangeably, since they both refer to the same mass spectrometer operating principle. For a matter of clarity we always use the term SRM throughout the text, but we always comprise both as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD or ETD.

Triple quadrupole instruments operated in SRM mode have been used for decades to detect and quantify small molecules (e.g. drugs or drug metabolites extracted from complex biological matrices). The first applications of SRM for the quantification of proteins were targeting one or few selected peptides.

There is a particular demand for reliable high sensitivity quantification of proteins from plasma to bridge the current gap between biomarker candidate discovery and validation. The high dynamic range of more then 10 orders of magnitude of proteins in plasma from albumin (35-50 mg/ml) to low abundance proteins like interleukin 6 (0-5 pg/ml) challenges current technology.

Lange et al, (Molecular and Cellular Proteomics 7.8, 1489-1500) discloses the use of MRM to probe responses of some *Streptococcus pyogenes* proteins to the presence of human serum. In this paper a "real" biological sample (a mixture of *Streptococcus* proteome digests) was used to validate and optimize MRM assays. Therefore all known problems related to using biological samples are taken into account.

Mayya et al. (Molecular and Cellular Proteomics 5.6, 1146-1157) purified and accurately quantified heavy labelled synthetic peptides are used to develop MRM assays. These purified heavy labelled peptides are very expensive. The purity of the peptides used in the cited paper is described as >80% and they are quantified which makes them expensive.

SUMMARY OF THE INVENTION

The object of the present invention is therefore to provide a method for the determination of an SRM assay for one or a multitude of peptides, a correspondingly determined assay as well as uses of such an assay.

The present invention correspondingly proposes a method for the determination of an SRM assay for one or more peptides and thus for the corresponding protein(s) of interest including the following steps:

(1) a protein of interest, a group of proteins of interest or a whole proteome, is digested/cleaved to form a mixture of peptides, from which, in a mass spectrometry experiment, at least one peptide is identified which is uniquely associated with the target protein and therefore reveals its quantitative behaviour under different experimental conditions. Optionally, such peptides are determined from samples in which specific classes of proteins or peptides may be selected by using appropriate purification/separation strategies (e.g. separation of a specific type or proteins like phosphoproteins or the like).
(2) this at least one peptide is synthesized/generated essentially without subsequent purification thereof;
(3) this at least one unpurified peptide is analyzed by selected reaction monitoring (SRM), preferably coupled to liquid chromatography (LC-SRM);
(4) development, validation and/or optimisation of the corresponding assay of the at least one peptide with determination of the (LC-)SRM coordinates for a protein of interest and/or of a regulator of interest.

The developed assays can then be applied to the detection and quantification of the peptide and/or protein(s) of in a sample(s) of interest Any kind of biological samples comprising peptides can be the starting point and be analyzed in the above procedure. Indeed any protein/peptide containing sample can be used for and analyzed by the assays produced here (cells, tissues, body fluids, waters, food, terrain, synthetic preparations etc) just to make simple examples. When in step (1) mentioning "a protein of interest, a group of proteins of interest or a whole proteome digested/cleaved to form a mixture of peptides", this shall therefore also include the use of peptide mixtures directly as the starting point for the method. In this case the step of digestion/cleavage is not necessary. The assays can also be applied to and/or based on any non-digested sample. E.g. if one is interested in screening small peptides already present in blood, is not necessary to digest/cleave the sample.

When in step (1) mentioning digestion/cleavage, this shall include any kind of cleavage strategies, be it enzymatic, chemical, physical or another mechanism of cleavage and combinations thereof.

When in step (2) mentioning that the peptide is synthesized/generated this shall include any kind of peptide production: unpurified peptides can e.g. either be synthesized and/or recombinantly derived or generated by any other chemical/biological/physical method. It is for example possible to synthesize a library of low cost peptides (e.g. by SPOT technology) and then perform some minimal purification/enrichment of the synthetic peptides, even altogether (for example one can do a phosphopeptide-enrichment on the synthetic phosphopeptides) to increase the purity somewhat, this is however not necessary. The term unpurified peptide shall therefore include also mixtures of peptides in which all of them are of interest and which does essentially not comprise constituents which are not of interest. Each of these peptides in a mixture is however the result of a synthesis (or generally a generation process) essentially without subsequent purification, or a group of proteins of such a mixture is the result of a common synthesis again essentially without subsequent purification. The term unpurified peptide shall however not be understood as meaning a mixture of different peptides, all of them being of interest, and each of them being introduced into the mixture in a purified form. This is specifically in contrast to what is disclosed in processes according to the state-of-the-art and as for example described in Lange et al (Lange et al., targeted qualitative analysis of *Streptococcus pyogenes* virulence factors by multiple reaction monitoring, molecular and cellular proteomics, 7.8, 1489), where a mixture of peptides is used, each of these peptides is however a purified peptide which has been purified after synthesis. Therefore unpurified peptide shall normally mean that there is a substantial fraction of constituents which are not of interest and which are leftovers from the synthesis process. Typically this impurity fraction is in the range of more than 1%, or even more than 5%, or in some cases even more than 30% or 50% compared with the peptide of interest.

In step (1) different experimental conditions are mentioned, the method is however also applicable to a situation where our is interested to have an assay for a peptide/protein that is not regulated e.g. to measure the content of a particular protein in waters/food.

Generally, as pointed out above, when talking about SRM this shall include SRM as well as modifications of these techniques as well as any analogous technique as outlined in the introductory portion above. For an overview over SRM techniques reference is made to e.g. the Article by Domon and Aebersold, in Science 312, 212 (2006), and the references cited therein, and as concerns this techniques the disclosure thereof is expressly included in the present specification.

A protein sample of interest can then be analyzed in SRM mode, optionally in time-constrained SRM mode, using specifically determined liquid chromatography elution times to trigger acquisition of the set of selected SRM traces, thus drastically increasing the throughput. The analysis allows to detect and eventually even quantify the set of proteins of interest.

This invention presents a method to develop sensitive and specific assays for proteins (in any case detected by means of peptides) or for peptides of interest. How one chooses the set of proteins/peptides of interest can vary. It can e.g. be a set of proteins that one wants to monitor in a sample because one knows from the literature to be functionally related (e.g. all proteins composing a known signalling/metabolic pathway); it could be a set of candidate protein biomarkers that one wants to screen in either a validation phase of a biomarker discovery project or that one already wants to screen in the blood of patients as markers of disease in a clinical phase; it could be a list of (phospho)peptides that one knows to be diagnostic of a given kinase activity that one wants to screen for any pharmaceutical/medical purpose; it could be a set of proteins that one hypothesises to be drug-targets and that one would like to screen after administration of different doses of the drug etc. This list is just to clarify that the selection of the proteins/putative markers/regulators etc is done at the front end of the invention, then the invention is used to develop assays to specifically monitor quantitatively the set of proteins/peptides in samples of interest and e.g. to optionally confirm the biomarker with a large number of samples, test/ design a drug, have an assays to monitor the marker at a clinical level etc.

The different experimental conditions of step (1) can be given by different origin and/or derivation and/or disease and/or regulation of one single desired protein and/or group of proteins of interest or whole proteome wherein preferably the different regulation is that the single desired protein and/or group of proteins of interest or whole proteome is based on influenced, modified and/or diseased cells, tissues and/or body fluids of an organism, wherein preferably the single desired protein and/or group of proteins of interest or whole proteome is based on a proteome derived from a genome in which a gene was knocked-out or mutated, and/or is based on a proteome in which a gene was knocked down or over expressed, and/or is based on a proteome in which the single desired protein or the group of proteins of interest were inhibited or activated by a biological, physical or chemical means, preferably by means of inhibitors or activators and/or is based on a proteome from diseased cells or tissues in which any gene or protein affecting signalling pathways was mutated and/or disregulated.

The group of proteins of interest may comprise one or several specific classes or types of proteins or peptides which are preferably separated/isolated/enriched by using isolation/purification/separation/enrichment steps, wherein preferably such a separation involves the separation of a specific type of proteins or of modified proteins such as e.g. phosphoproteins and/or glycoproteins and/or sulphorylated proteins (or in case of peptides as the starting material selection of the corresponding types of peptides/modified peptides).

In a first preferred embodiment of the present invention, the method is further characterised in that the unpurified peptide is either synthesised in step (2) on a micro-scale, preferably by using solid-phase synthesis (e.g. the spot-synthesis technology, Hilpert K, et al. Nature Protocols 2,—1333-1349 (2007)) or recombinantly expressed or derived by digesting/cleaving recombinantly expressed proteins that contain the peptide sequence of interest without subsequent purification (e.g. by chromatographic methods). Proteins that contain parts or the whole target protein/peptide sequence can thus be recombinantly expressed for instance in bacterial hosts or mammalian cell lines. Preparations of these recombinantly expressed proteins are then digested. Thereby a variety of peptides is released that can be used to derive SRM coordinates. Each of them is basically an unpurified peptide as previously discussed. Indeed the use of unpurified peptides astonishingly this is possible, in contrast to the expectation of the person skilled in the art, who would assume that optimisation and establishment of a specific assay is only possible by using the peptides of a sample of clean and specifically synthesised peptides. It is possible to use unpurified peptides for the establishment of the parameters for the assay. Indeed the extremely high specificity of the LC-SRM method used allows to determine the assay in spite of impurities being present in a correspondingly synthesised peptide as the impurities do not influence the determination process. This allows a determination process at much higher throughput using high-speed synthesis of peptides without the burdensome need of a cleaning processes for the peptides and at drastically reduced costs.

Normally this means that in case unpurified peptides are made in step (2) and/or used in steps (3) and/or (4) the peptide of interest is present in these peptide preparations for the method in amount which could be less than or even far less than 99% or preferably 98%, or even 95% of the total sample (percent calculated as weight percent of solid content). The expression "unpurified" as used in the specification and in the claims shall generally not exclude samples which have been partly purified. The expression "unpurified" shall therefore also includes samples which have been partly purified but in which the peptide of interest is present in amount less than or even a far less than 99% or 98%. The lower limit of purity is essentially determined by the signal detection range (also called dynamic range) of the mass spectrometer. At present mass spectrometers have a range of detection of maximum 6 orders of magnitude, but in the future this can be extended. This means that the lower end of the required purity can be as low as 0.0001%-0.00001% or even lower. Also the detection limit depends on the peptide sequence: some peptides "respond well" in the mass spectrometer and therefore one can still detect them when they have a much lower purity (e.g. <0.00000001%).

Normally the unpurified peptides are present in an amount of more than 0.1%, normally more than 5%, and preferably more than 10%. It is indeed possible to work with peptide of interest contents of below 98%, or below 95% or below 90 or 80%. The further constituents of the unpurified peptide samples used in the steps can be e.g. side products of the synthesis, like for example different peptides not identical to the peptide of interest or derivatives of the peptide of interest with reactants of the synthesis if the peptide is synthesized, or a mixture of other peptides, intact proteins or other cellular components, if the peptides is derived from recombinant protein/peptide expression.

According to a further preferred embodiment, in step (3) fragmentation spectra can be additionally acquired to validate the assay or to select suitable peptide fragments.

It is, as outlined above, not absolutely necessary that in step (1) indeed a specific protein of interest, group of proteins of interest or proteome is actually digested to generate the corresponding SRM assay. It is also possible to use the above approach just for the determination of an assay for a specific protein of which one already knows/predicts the corresponding peptide fragments. Correspondingly therefore in step (1) it is also possible that use is made of prior proteomics datasets or of bioinformatic prediction such as by screening large proteomics data repositories (such as PeptideAtlas, see e.g. Deutsch, E. W. et al. Human Plasma PeptideAtlas. Proteomics 5, 3497-3500 (2005), literature or of computational prediction of the MS detectability, using algorithms for determining peptides/proteins of interest (such as PeptideSieve, see e.g. Mallick P, et al. Nat. Biotechnol. 2007 January; 25(1): 125-31.).

According to another preferred embodiment, in step (4) at least one of the group of the following parameters of the assay is determined: best responding peptides, corresponding elution times of the liquid chromatography (inter alia depending on the corresponding stationary phase), best responding fragments, fragment intensity ratios, optimal collision energies/collision gas pressure, declustering potentials, so essentially all the optimal parameters to maximize sensitivity and/or specificity of the assays, to allow for an efficient timing of the detection process in the final detector and the three quadrupoles parameters of the SRM set up. Indeed the set of coordinates to detect and quantify the protein of interest defining the SRM assay is determined.

It should be noted that the actual determination of the an individual assay does not necessarily have to be carried out for each peptide in a separate analysis, but can, according to a preferred embodiment, be determined in parallel, in a single analysis, starting from a mixture of peptides of interest, each of them or altogether resulting from an unpurified synthesis.

Often quantification and not only qualification of the peptides and/or of the corresponding proteins or activity of the corresponding proteins/regulation of the corresponding proteins is desired.

This can for example be achieved in that after step (4) a heavy-labelled analogue of the selected peptide is synthesised to be used as an internal standard to achieve absolute quantification of a protein of interest.

According to a preferred embodiment, for the absolute quantification of a protein of interest at step (2) or after step (4) the following steps are implemented:

(5) the protein/peptide of interest (or a whole group or range of proteins) is synthesized/generated without subsequent purification in a tagged-form preferably with a heavy labeled amino acid at the C-terminus, and the unpurified tagged-peptide is then subjected to cleavage and/or (enzymatic) digestion under release of the quantification tag in a stoichiometric amount to the peptide of interest;

(6) addition of a quantified heavy-labelled peptide analogue of the tag to the peptide sample in known amount and the tag and correspondingly the peptide of interest is quantified by mass spectrometry;

(7) addition of the accurately quantified, heavy-labelled peptide(s) to a protein sample and validation and/or optimisation of the SRM assay(s) for the corresponding proteins using the above steps (1)-(4) to achieve absolute quantification of the endogenous levels of the proteins.

Again, when in step (5) mentioning digestion/cleavage, this shall include any kind of cleavage strategies, be it enzymatic, chemical, physical or another mechanism of cleavage and combinations thereof. Also again in step (2) mentioning that the protein/peptide of interest is synthesized/generated in a tagged form this shall include any kind of peptide/protein production: proteins/peptides can e.g. either be synthesized and/or recombinantly derived or generated by any other chemical/biological/physical method.

For example the tag in step (5) can be a fluorophore and/or a short amino acid sequence which is added to the sequence of each peptide of interest, separated by a site of specific ( ) cleavage such as tryptic cleavage, other cleavage enzymes however also equivalently being possible the tag being adapted thereto.

Indeed this very simple and efficient quantification technique, which does not necessitate quantified samples of each peptide but only makes use of a tag which has to be available in a quantified manner, is extremely efficient. The general idea behind it is to actually tag the peptide of interest with a quantification tag and benefit from the fact that it is possible to relieve a tag from the peptide of interest in a stoichiometric manner by digestion/cleavage. Comparison of the signal intensity of the released quantification tag, e.g by mass spectrometry, with that of a defined amount of an isotopically labelled form of the quantification allows simultaneous measurement and relative computation and thereby quantification of the peptide and correspondingly indirectly quantification of the protein from which the peptide results. The same quantification tag can be attached to different peptides, and therefore for a large number of peptides to be quantified, which allows to use the same tag, also the same quantified heavy-labelled tag can be used for their quantification.

As mentioned above, according to another embodiment, a plurality of assays each for individual peptides of interest can be determined according to steps (1)-(4). It is correspondingly possible to determine a complete overall assay for example for a proteome including a vast list of individual assays for individual peptides characterising uniquely individual proteins or a set of closely related proteins (e.g. protein isoforms). Unique characterisation can for example be understood in the sense that they are unique for a specific regulation of a protein, so it is for example possible that peptides are unique in that they are characterising in an unambiguous way, so without overlap with other signals, for one single protein and a modified or regulated form thereof. So the peptide is selected such as to be sensitive to a protein modification (mutant) or regulation (for example influencing by a pharmaceutical) and the corresponding SRM being sensitive to changes between these two types.

Time-constrained/scheduled SRM acquisition is only one of the possibilities provided by the present invention, and is one (but not the only) way of sample analysis, but is a very efficient way to increase the number of assays measured in a single run (more than 1000 transitions can be measured in one run). One can also use the assays developed with the presented method without scheduling of SRM traces acquisition, if interested in not many proteins. Obviously scheduling is much better, but in case some mass spectrometers or the associated software do not allow for performing scheduled SRM, working without scheduling is also an option within the invention. In a preferred embodiment a protein sample of interest (can also be a full proteome) is analysed using at least one, preferably a multitude of assays for peptides of interest as determined using a method as described above, wherein time-constrained SRM is used and adapted elution times according to the assays are used to trigger acquisition of the set of selected SRM traces according to the assays. The time constrained-acquisition of SRM traces allows to increase the throughput by measuring a higher number of SRM transitions/analytes of interest (more than 1000) in a single LC-SRM analysis.

According to a preferred embodiment of this method of analysis, the method is used for the analysis and/or comparison of protein samples of wild-type or physiological/healthy or unregulated origin with protein samples of mutant or pathological or regulated origin, wherein preferably regulation is induced by a pharmaceutically, chemically or biologically active substance.

As mentioned above, absolute quantification can be desirable. To this end, the method of analysis can be characterised in that for absolute quantification of a protein of interest (5) the protein(s)/peptide(s) of interest is synthesized without subsequent purification in a tagged-form preferably with a heavy labeled amino acid at the C-terminus, and the unpurified tagged-peptide is then subjected to cleavage and/or (enzymatic) digestion under release of the quantification tag in a stoichiometric amount to the peptide of interest;

(6) a quantified heavy-labelled peptide analogue of the quantification tag is added to the peptide sample in known amount and the tag and correspondingly the peptide of interest is quantified by mass spectrometry; and (7) the accurately quantified, heavy-labelled peptide(s) is added to the protein sample to achieve absolute quantification of the peptide (s) of interest and thus indirectly of the endogenous levels of the proteins of interest.

The present invention furthermore relates to an assay determined using to a method as detailed above. In particular the invention relates to assays comprising at least one peptide according to SeqID 4-SeqID 179, wherein these assays are used for the identification of the corresponding protein as given in the table further below. Preferably for each protein more than one peptide according to this table is used, and in assays for the determination of several peptides in parallel several of these peptides are investigated.

Furthermore the present invention relates to the use of such assays for the quantitative analysis of a protein sample, wherein SRM or time-constrained SRM are used and adapted elution times and possibly further parameters according to the assays are used to trigger acquisition of the set of selected SRM traces according to the assays.

Last but not least it relates to a pharmaceutically, chemically or biologically active substance determined using a method as given above.

Further embodiments of the present invention are outlined in the dependent claims.

SHORT DESCRIPTION OF THE FIGURES

In the accompanying drawings preferred embodiments of the invention are shown in which:

FIG. 1 is an illustration of an SRM/SRM analysis on triple quadrupole mass spectrometers: several analytes are coeluting from the chromatographic system; the specific m/z selection in the first quadrupole filters out most coeluting ions; however, due to identical mass, interfering ions might remain; in quadrupole 2 the analytes are fragmented; the m/z selection in the third quadrupole filters out all the fragments of the analyte selected in step 1 and transmits only a particular fragment of the analyte for specific detection;

Figure 4:
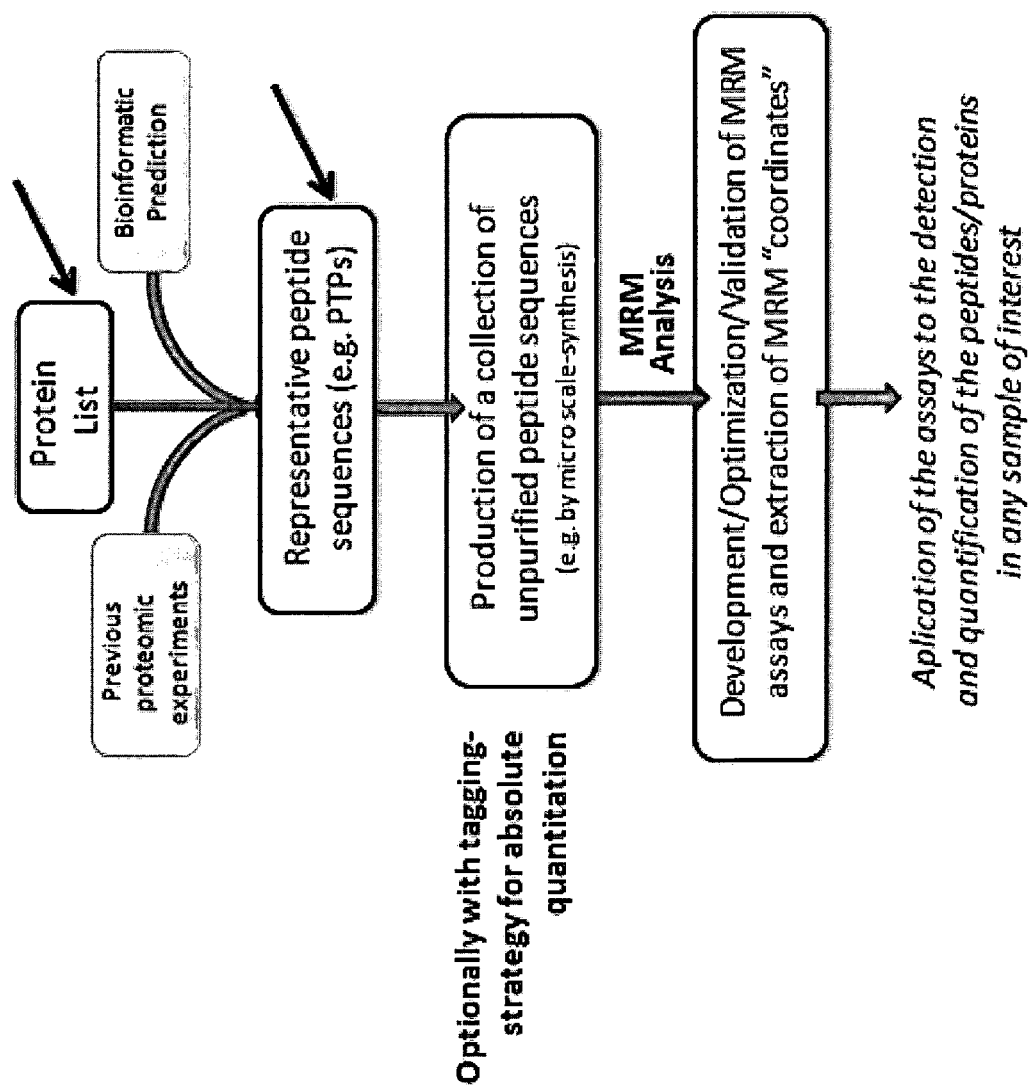
Figure 5:

FIG. 4 shows a flow diagram of the rapid approach using unpurified peptides; and FIG. 5 a) shows an SRM assay for an unpurified synthetic peptide, analysed in a complex peptide mixture, and b) an example of high-throughput protein quantification by SRM, wherein each peak represents an SRM assay established and validated with the use of unpurified synthetic peptides (in the example one thousand SRM assays are recorded in less than one hour of LC-SRM analysis).

DETAILED DESCRIPTION OF THE PREFERRED EMBODIMENTS

In the following the invention shall be described in more detail with reference to the figures. The description is for the purpose of illustrating the present preferred embodiments of the invention and not for the purpose of limiting the same.

This description specifically details the application of SRM/MRM technology for proteomics in particular for quantitative proteomics. It describes the setup of a proteomic SRM/MRM experiment, including the selection of proteotypic peptides and the generation and validation of optimized peptide specific transitions. Furthermore, different aspects influencing sensitivity and precision of quantification by SRM/MRM are discussed. Finally, examples of successful applications of SRM are given to illustrate its unique potential for reproducible, quantitatively accurate proteomics.

Selected/Multiple reaction monitoring (SRM/MRM) is a promising technique with the potential to alleviate, at least in part, many shortcomings of current shotgun proteomics:

The simplest approach to quantification of analytes of interest from LC-MS data is the use of eXtracted Ion Chromatograms (XIC). Data are collected in full MS scan mode and processed post-acquisition to reconstruct the elution profile of an ion of interest, using its m/z value and a tolerance window for the extraction. The XIC plot shows the ion current resulting from the selected mass range as a function of chromatographic retention time. XIC peak heights or peak areas are used to determine the analyte abundance. Selected/single ion monitoring (SIM) is a scanning mode in which the mass analyzer is set to scan over a narrow mass range centered on the m/z value of an ion of interest. The narrower the mass range the more specific the SIM assay. SIM experiments are more sensitive than XICs from full scans because the mass spectrometer is allowed to dwell for a longer time over a small mass range of interest. Different ions with m/z values within the selected mass range however are not discriminated and result in a cumulative signal in either SIM scans or XICs.

Selected reaction monitoring (SRM) is a non-scanning technique, generally performed on triple-quadrupole like instruments and using collision-induced dissociation as a means to increase selectivity. In SRM experiments two mass analyzers are used as static mass filters, to monitor a pair of precursor/fragment ions characteristic of the analyte of interest. The selectivity resulting from the two filtering stages combined with the high duty cycle results in quantitative analyses with unmatched sensitivity. The specific pair of m/z values associated to the precursor and fragment ions selected is referred to as a "transition" and can be written as parent m/z>fragment m/z (e.g. 673.5>534.3). By definition SRM experiments can be performed on all mass spectrometers capable of MS/MS experiments—e.g., on ion traps, by scanning a narrow mass range in MS2 mode, centered on a fragment ion specific to the precursor of interest. However, the full potential of SRM as described here is optimally tapped when the experiment is performed in triple quadrupole mass spectrometers.

Multiple SRM transitions can be measured within the same experiment on the chromatographic time scale by rapidly toggling between the different precursor/fragment pairs. Typically, the triple quadrupole instrument cycles through a series of transitions and records the signal of each transition as a function of elution time. The method allows for additional selectivity by monitoring the chromatographic coelution of multiple transitions for a given analyte. The term multiple reaction monitoring (MRM) is frequently used to describe the parallel acquisition of multiple SRM transitions, but it is deprecated by the IUPAC nomenclature (current Provisional Recommendations, K. K. et al., Standard definitions of terms relating to mass spectrometry, IUPAC Current provisional Recommendations, 3rd Draft Document, August 2006).

Figure 1:
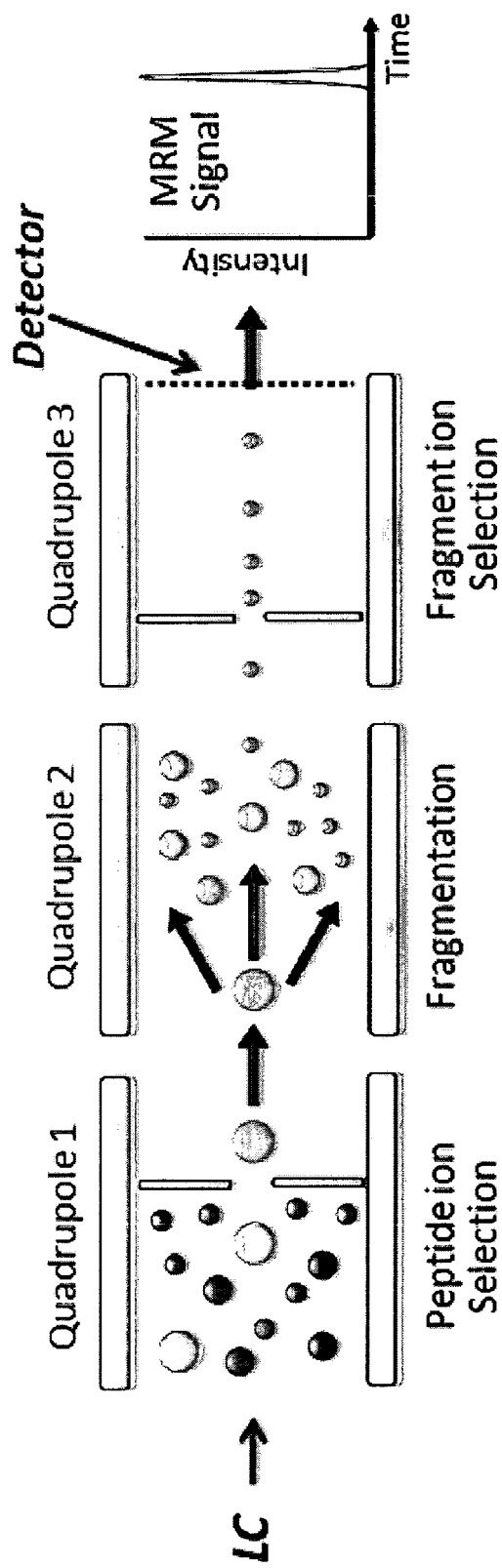

SRM exploits the unique capabilities of triple quadrupole mass spectrometers for quantitative analysis. During SRM measurements, the first and the third quadrupole of the mass spectrometer are operated as selective mass filters, that specifically isolate a peptide ion and a corresponding fragment ion, respectively, while the second quadrupole serves as linear collision cell (FIG. 1). Unlike common MS based proteomics, no mass spectra are recorded in a quantitative SRM analysis. Instead, the detector acts as counting device for the ions matching the criteria specified at the level of first and third quadrupole thereby returning an intensity value over time. SRM based quantification performed on a triple quadrupole mass spectrometer is characterized by high selectivity for the targeted molecule (1), high sensitivity (2) and a linear response over a high dynamic range (3) of up to five orders of magnitude. (1) The selectivity arises from the two stage narrow mass filtering at the level of precursor and fragment ions. In particular for the detection of proteins of low abundance in highly complex mixtures such an increased specificity is crucial for successful quantification. (2) The sensitivity arises from (a) the high ion yield of triple quadrupole like mass spectrometers and (b) the high duty cycle—the fraction of time the detector spends on quantifying a particular ion—which results from the non scanning nature of SRM measurements. (3) The high duty cycle also brings forward a high dynamic range which is not diminished by coeluting ions of a different m/z.

Selectivity, sensitivity and dynamic range make triple quadrupole mass spectrometers ideally suited for the current and future challenges of proteomics for systems biology: Sets of proteins, including low abundant ones, need to be accurately quantified from multiple highly complex samples in a reproducible manner.

SRM Applied for Quantitative Proteomics:

To overcome the limitations of classical shotgun proteomics techniques, (including lack of sufficient sensitivity and comprehensiveness) an alternative, targeted, proteomic approach was developed, which exploits the power of SRM. In contrast to a shotgun experiment, SRM based experiments are strictly targeted. The MS instrument will only quantify peptides that specifically have been selected. That requires a different workflow from conventional MS experiments. This is based on a series of steps, which include:

1. First, proteins of interest have to be selected as targets for quantification.
2. Then, unique peptides need to be determined for each target protein, ideally showing the highest mass spectrometry signal response, to maximize the sensitivity of the protein assay. This task can be complicated by vastly unequal MS signal responses for the peptides generated from a target protein and the observation that many peptides are common to multiple proteins and thus unable to identify a protein.
3. For each fragment ion predominant fragments specific to the peptide of interest, have to be derived, to be used as SRM transitions. The sensitivity of SRM based experiments is highly dependent on a good selection of precursor and fragment ions combinations (transitions). The time required to establish these specific transitions is the price to pay for the excellent quantitative performance of SRM based experiments.
4. The precursor/fragment ion transitions need to be validated to confirm the identification of the peptide of interest, for example by acquiring a full MS2 spectrum of the peptide or by coelution with a reference peptide.
5. For each peptide-fragment pair, a number of MS-specific parameters is optimized (e.g. collision energy, collision gas, declustering potential), to maximize the signal response/sensitivity
6. The "coordinates" of the final SRM assay are extracted, to be used in further analyses. Such coordinates include: the selected peptide, the selected peptide fragments, the corresponding mass-to-charge ratios, the corresponding elution times to be optionally used in time-constrained SRM acquisition, fragment intensity ratios, optionally as derived from a full fragmentation spectrum, collision energies, declustering potentials and more in general any MS specific parameter aimed at maximizing the sensitivity and specificity of the assay.
7. Optionally: heavy-labelled analogues of the selected peptide are synthesized to be used as an internal standard, to achieve absolute quantification of the protein of interest
8. The optimized and validated SRM assay(s) are applied to the detection and/or quantification of the peptide/protein(s) in any sample(s) of interest. The sample(s) is/are enzymatically digested with an enzyme that produces the peptides selected (e.g. trypsin) and analyzed by LC-SRM, using the assays developed.

This approach based on SRM allows to detect and accurately quantify specific peptides in complex mixtures, and thus the corresponding proteins, at a drastically higher sensitivity (in the low attomole range) and specificity compared to classical proteomic techniques. It can be shown that proteins spanning the whole range of protein expression in cells (six orders of magnitude) can be detected and quantified by SRM. However, despite these favourable performance characteristics SRM has not yet been broadly applied in proteomics. One main reason for this is the effort required to establish a SRM assay for every protein, highlighted by the previously described workflow steps. This is a rather elaborate and iterative series of operations, which can be based on a trial-and-error approach, in the absence of previous knowledge about the mass spectrometric behaviour of all possible peptides specific to a protein. The steps are further constrained by the typical duty cycles of SRM experiments which do not allow high numbers of peptides/peptide fragments to be tested in one analysis, if no previous information is available about the peptides. This overall procedure can require several days for a protein SRM assay to be established. Furthermore the required validation step, generally done by acquiring a full fragmentation spectrum of the peptide, does often not allow to fully exploit the sensitivity of the SRM technique. Last, the prohibitive cost of highly pure, accurately quantified heavy labelled peptides further affects the throughput and the possibility of multiplexing. For these reasons the power of the SRM approach has not been exploited yet and successfully applied to e.g. the fields of drug and biomarker discovery, and it is currently used to analyse only small subsets of proteins, mostly in the context of academic research, with large efforts.

The presented invention deals with such issues by providing a method for the high-throughput and cost-effective development and validation of quantitative SRM assays for a whole proteome or subproteome. It thus supports the use of SRM as a novel platform for high-throughput quantitative proteomics, allowing to exploit the drastically higher sensitivity and specificity of this technique for the analysis of thousands of proteins in a reasonable amount of time.

Figure 2:
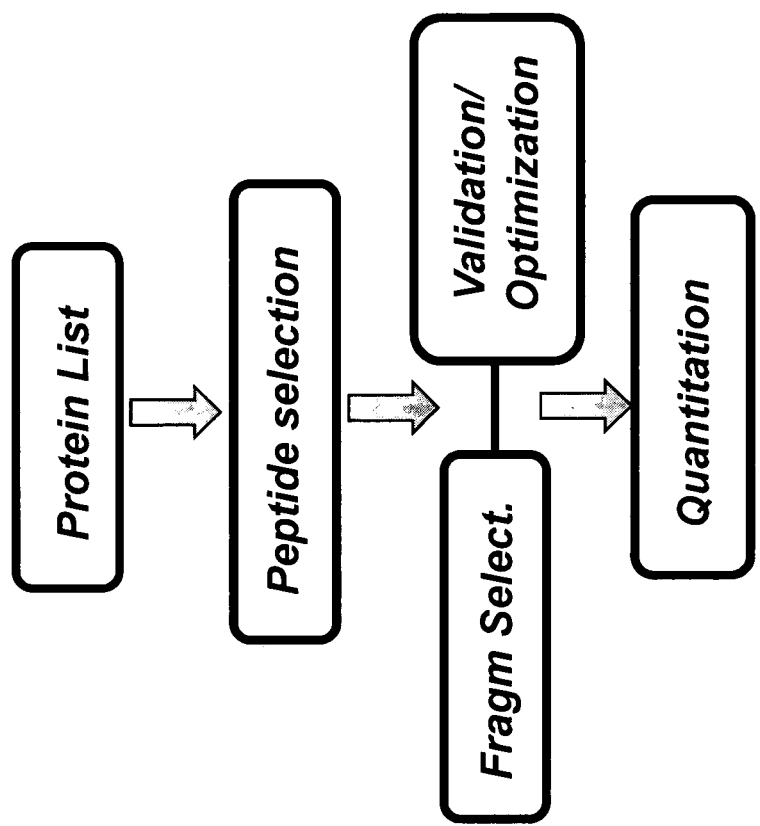
FIG. 2 shows a general workflow of SRM-based proteomic experiments.

Detailed Description of the Individual Steps:

The following paragraphs guide through the additional details of some of the above mentioned general steps (1)-(8) of an SRM experiment (see also FIG. 2).

(1) Targeting Proteins:

The first step in a targeted experiment is the selection of the proteins of interest. The proteins selected can also be proteins which are functionally related, candidate biomarkers, drug targets etc, as outlined above. This list of proteins can be based on previous experiments or on the scientific literature. Databases combining protein-protein interaction data with other evidence are a good source to identify all proteins belonging to a pathway of interest. Alternatively, network expansion can be used to complement a set of proteins (as e.g. implemented in PhosphoPep, Bodenmiller B et al, Mol Syst Biol 3: 139). In addition to these proteins of interest several "housekeeping" proteins can be selected for normalization purposes, to be able to correct for uneven total protein amount in the samples. A few regulated proteins in this group do not interfere with normalization as long as the group is sufficiently large (>10 proteins) and outlier insensitive statistic is applied.

(2) Selection of Peptides:

Each of the targeted proteins yields tens to hundreds of peptides upon digestion. Only few representative peptides per protein are usually targeted to retrieve the protein quantity. For the success of the SRM experiment it is therefore essential to choose the well observable, unique peptides whose quantification is not impaired by unpredicted modifications.

Proteotypic peptides (PTPs): Only a subset of peptides ionizes efficiently in ESI-MS. How can these well observable proteotypic peptides (PTPs) be identified? Although all peptides could be individually tested, it significantly decreases the required instrument time to preselect a subset of peptides based on previous observations in previous proteomic experiments. For a growing number of organisms a significant number of MS experiments has been performed and the data is deposited in online repositories which support the retrieval of PTPs for the proteins of interestA valuable complement to these experimentally based sources are computational tools which predict the proteotypicity of peptides based on the amino acid composition. These help to target the most likely observable peptides even if the particular protein has not been detected before.

Uniqueness: When selecting peptides, it is important to choose peptides which uniquely represent the targeted proteins. Therefore, peptides which can be derived from different genes should be excluded, unless the cumulative quantification of the pool of the corresponding proteins is of interest. Sometimes it might in addition be required to select peptides which can distinguish different splicing isoforms or SNPs which is straightforward if the discriminating peptides are well detectable.

Post translational modifications: Modified peptides will not be detected by SRM unless specifically targeted. Quantitative differences may therefore be a result of differential modification and not differential protein abundance. The reproducible differential regulation of two peptides from the same protein is indicative for a posttranslational modification of one of the peptides. On the other hand, SRM can be used to specifically target and quantify peptides with posttranslational modifications like phosphorylation, methylation or acetylation.

Chemically induced modifications: Care should be taken to avoid peptides which might be unspecifically modified in the cell or during sample processing as this could introduce considerable variation. In particular methionine containing peptides should be avoided as these get oxidized to varying degrees. Peptides containing tryptophane or alkylated cysteine may also get oxidized. Further, peptides containing glutamine or asparagine may be chemically unstable and convert to glutamate or aspartate depending on the surrounding sequence.

(3) Selection of Transitions:

For the quantification of a peptide by SRM, specific m/z values for the first and third quadrupole need to be selected. We refer to the combination of these values and associated parameters as "transition". The m/z value of the first quadrupole is determined by the mass and the predominant charge state of the peptide ionIn the third quadrupole a particular fragment ion of the peptide is selected. The m/z value of the third quadrupole is determined by the mass and the predominant charge state of the fragment ion selected in the transition. Peptides with good MS signal response and the corresponding predominant, specific fragments are ideally selected, to maximize the sensitivity of the assay. The fragment ion masses of the target peptide can be calculated and experimentally tested in LC-SRM mode on a triple quadrupole instrument. This results in an overlay of SRM traces of different intensities, and with perfectly aligned intensity peaks in a retention time scale. The SRM transitions resulting in the most intense peaks can then be selected to be used as final assay for the peptide of interest, thus maximizing the sensitivity of the assay. However, if different ion series are taken into account, and more than one precursor charge state, this can result in more than 30 transitions per peptide to be tested. This high number of transitions, coupled to the typical SRM cycle time constraints, result in a limited number of peptides for which transitions are tested in a single LC-SRM analysis. Alternatively, MS/MS spectra for the target peptide can be acquired on a triple quadrupole instrument to derive optimal SRM transitions.

(4) Validation of Transitions:

Before starting the quantitative SRM experiment, it needs to be ensured that the acquired data will specifically reflect the quantity of the targeted peptides. Therefore, in the validation phase, MS2 spectra are acquired to ensure the specificity of the transitions The acquired MS2 spectra are compared to the predicted peptide fragments to validate that the major MS2 peaks are matched.

If confirming MS2 spectra are available from other instruments with the same chromatographic setup, the retention time can be used as important additional constraint. Also, the monitoring of several peptide fragments which display a common intensity peak helps to assure specificity. Alternatively transitions can be validated by coelution with synthetic analogues of the peptide of interest.

Figure 3:
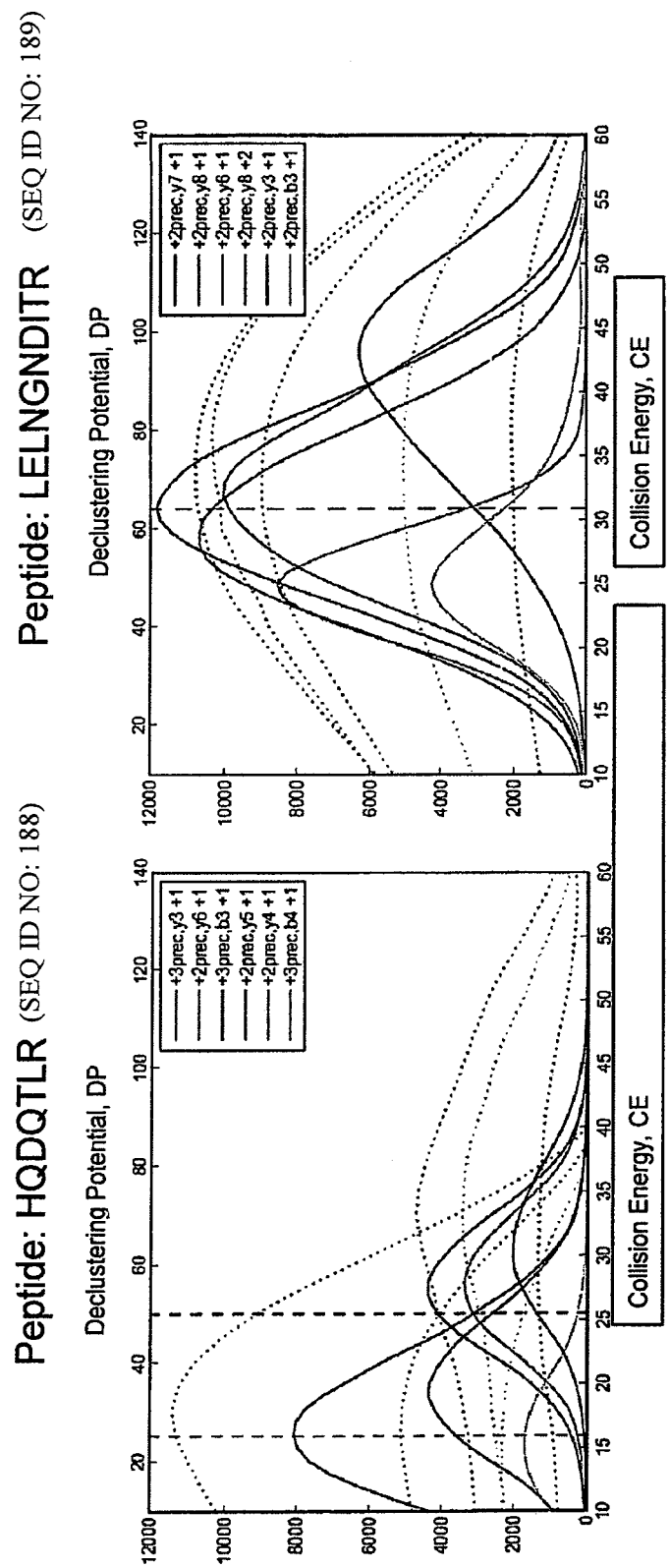
FIG. 3 shows an optimization of SRM transitions with respect to collision energy and declustering potential: plot of intensity versus collision energy (CE, solid lines) or declustering potential (DP, dotted lines) for the 6 best transitions of 2 peptides; the predicted CEs for the doubly (at 17 and 31) and triply (at 26) charged precursors are marked by vertical dashed lines.

(5) Optimization of Transitions:

The transitions used during the validation phase might not be performing at their maximum sensitivity transitions for a particular peptide. To further increase the sensitivity, several parameters can be optimized as they influence signal intensity. Among them:

Collision energy: With increasing collision energy a larger part of the precursor ions is fragmented and fragment ion intensity increases until this increase is overcompensated by the loss due to secondary fragmentation events (FIG. 3). This optimal collision energy is approximately linearly correlated with the precursor mass for a given charge state. However, particular peptides or fragments deviate considerably from the predicted value. We found that individually optimizing collision energy and declustering potential increased signal response 2 to 5 fold for every sixth transition. The collision gas pressure in the collision cell can also be optimize with effects similar to those of the collision energy.

Ion source parameters: During the ionization process, single ions need to be generated. The declustering potential (DP) supports this process by dissociating ion clusters and solvent molecules. However, at too high DP peptides are fragmented. From plotting many experimentally determined DP optima, a positive linear correlation of precursor m/z value and DP optimum can be determined (6) Quantification:

Upon validation and optimization of transitions, the targeted proteins can be quantified by SRM analysis in multiple samples. In SRM mode, the instrument can repeatedly cycle through a list of transitions spending a defined time, the dwelltime, for each transition. For example, targeting one peptide with 5 transitions of 200 ms dwelltime would result in a cycle time of 1 second (5×200 ms). Thus, every second an intensity value would be recorded for each of the transitions. Targeting 50 peptides with 3 transitions of 10 ms dwelltime each would result in a list of 150 transitions and a total cycle time of 1.5 seconds. Even when analyzing more than hundred transitions with dwelltimes of 10 ms or less, the fraction of time spent for each transition, the duty cycle, compares very favorable to full scanning mass spectrometric setups. The high duty cycle is one of the reasons for the unmatched sensitivity of SRM measurements. However, increasing the number of transitions decreases the respective dwelltimes at a fixed total cycle time. A successful strategy to increase the number of targeted peptides without decreasing individual dwelltimes and sensitivity is to restrict the acquisition of particular transitions to a window around the elution time of the targeted peptides. Using such a scheduling of SRM acquisition, the full cycle time is deployed to detect and quantify the currently eluting peptides. Depending on gradient length, elution peak width and reproducibility of chromatography this enables increasing the number of transitions by a factor of 5 to 20 without a decrease in dwelltime and sensitivity. The time constrained acquisition of SRM traces allows to quantitatively monitor more than 1000 transitions in one single LC-SRM analysis.

Quantification using stable isotope labeling: Quantification can be based on the ion current of the analyte or on the relative ion current of the analyte and an isotopically labeled internal standard. Quantification based on the ion current of the analyte alone can be used although it is sensitive to (1) drifts in spray efficiency over many runs or (2) matrix effects—ion suppression or enhancement due to coeluting substances. Therefore, the application of an isotopically labeled internal standard is generally recommended if precise quantitative results are aspired from the analysis of multiple samples. Most labeling approaches applicable for quantitative shotgun proteomics can likewise be used for SRM based quantitative experiments. As in shotgun proteomics, the earlier the isotopic label is introduced in the processing workflow, the more steps can be controlled. Isotope labeling of samples allows precise relative quantification. However, absolute quantification of proteins by SRM requires isotopically labeled peptides or proteins which are spiked in defined amounts into the sample. The signal of the endogenous peptide is then compared to that of the heavy-labelled standard, and the absolute amount of the endogenous peptide/protein is calculated. The highly pure synthetic peptides need to be accurately quantified, preferably by amino acid analysis (AAA). Besides the opportunity for absolute quantification, spiking synthetic peptides has several advantages: In contrast to whole proteome labeling approaches the amount of spiked in peptides can be adjusted to well detectable levels. In addition, the addition of heavy-labelled analogues facilitates the detection of low abundant peptides in highly complex mixtures. Endogenous peptides detectable only with minor, close to background signals can be accurately quantified if the elution profiles of several transitions from heavy and light version are aligned and if the ratio of the transitions is constant. This ensures that the quantitative results are not distorted by unspecific signals, for peptides detected close to the noise levels.

While the application of isotopically labeled peptides is the first choice from an experimental point of view, the costs of synthesis, purification and quantification of such peptides act often prohibitive for larger studies where more than a dozen proteins are to be targeted. Even though prices can be expected to decrease with increasing demand, the quantification of more then 100 proteins will presumably still require a considerable investment in the near future.

To summarize the present invention provides a further improved method for the high-throughput and cost-effective development and validation of quantitative SRM assays for a whole proteome or subproteome as detailed above. It is based on the use of libraries of low-cost unpurified peptides, synthesized, generated or recombinantly derived, to be used as a reference for deriving the final coordinates of an SRM assay, validating and optimizing the assay and optionally achieving absolute quantitation of the protein of interest. This is schematically illustrated as a flow diagram in FIG. 4. Input of this Figure indicated by the arrows is any list of proteins/peptides for which specific and sensitive assays are required.

The further improved approach consists of the following steps:

(1) For the proteins of interest (optionally a whole proteome) a set of possible unique peptides is selected. The selection can be facilitated by the existence of prior proteomics datasets or by bioinformatic prediction (the peptide selection can be already restricted to a few peptides known to have good MS properties, by screening large proteomics data repositories, such as PeptideAtlas, existing literature or by computational prediction of the MS detectability, using algorithms like PeptideSieve).

(2) The peptides are produced in an unpurified form, either by synthesizing them on a micro-scale (e.g. via the SPOT-synthesis technology) or recombinantly expressed or by digestion of the corresponding recombinantly expressed proteins and (3) they are analyzed by liquid-chromatography-coupled multiple reaction monitoring (LC-SRM), optionally acquiring fragmentation spectra to select suitable peptide fragments. If no fragmentation spectra are acquired several calculated fragments of the peptides are tested for the signal response in SRM mode. The peptides are optionally pooled and optimized in the same LC-SRM analysis.

(4) the analysis allows to directly validate the assay and to extract the SRM coordinates for a protein of interest, such as: best responding peptides, corresponding elution times, preferred charge state, best responding fragments, associated optimal SRM transitions, fragment relative intensities, optimal MS parameters such as collision energies, declustering potentials, collision gas pressure, etc.

(5) A protein sample of interest is then analyzed SRM mode, ideally in a time-constrained mode, i.e. using elution times to trigger acquisition of the set of selected SRM traces, thus drastically increasing the throughput. The analysis allows to detect and quantify the set of proteins of interest.

Optionally, if absolute quantification is to be achieved or in case internal standards are needed, the peptides (6) are initially synthesized in a tagged-form. A short amino acid sequence (quantification tag) is added to the sequence of each peptide of interest (ideally at the N-terminus), separated by a site of specific (enzymatic) cleavage (e.g tryptic cleavage) and the tagged-peptide is synthesized as previously described, ideally with a heavy labeled amino acid at the C-terminus. The unpurified tagged-peptide is then subjected to enzymatic digestion (7) and the quantification tag is released in a stoichiometric amount to the target peptide.

(8) A heavy-labelled peptide analogue of the quantification tag is spiked in the peptide sample in known amount and used to accurately quantify the tag—and therefore the target peptide,—ideally by mass spectrometry (the heavy-labelled peptide analogue of the quantification tag can be also spiked in before the digestion)

(9) Then the accurately quantified, heavy-labelled peptides are added to a protein sample and used to validate and optimize the SRM assays for the corresponding proteins (as previously described) and also to achieve absolute quantification of the endogenous levels of the proteins, in fast and high-throughput manner.

An example of the tagging strategy used for absolute quantitation of the peptides shall be given in more detail. In the example the enzyme trypsin is used (specifically cleaving after K or R residues; K indicates the heavy labeled amino acid (may also be another quantifiable tag such as a fluorophore), characterized by a mass difference of e.g. 8 Da):

```
Target peptide: ASDFGVNITEDVK
```

This is the peptide of interest sequence mentioned in above step (6), it can be provided in unpurfied form. It is preferably labelled at the right C-terminal K.

Quantification Tag (same for all peptides): TAGK

This is the short amino acid sequence which is added to the peptide of interest in step (6). This tag is not labelled and not quantified.

```
Synthetic Peptide: TAGKASDFGVNITEDVK
```

This is the result of the synthesis in step (6) and is the heavy-labelled tagged peptide of interest used in above step (7).

```
                                        (SEQ ID NO: 2)
Accurately quantified tag (int. standard): TAGK
```

This is the heavy-labelled peptide analogue of the tag of interest. It is labelled at the C-terminal K, and it is accurately quantified (and thus expensive). This is the most expensive element because it is quantified but it can be universally used for all target peptides which is an enormous advantage of the proposed method.

Indeed always the same tag is used for each of the peptides of interest, in this case the tag TAGK (SEQ ID NO:2). One can, for all these peptides of interest, use the same accurately quantified tag as an internal standard. The quantification of the peptide of interest can be easily obtained by a comparison of the signal intensity of TAGK (SEQ ID NO:2); (unlabelled) with TAGK (SEQ ID NO:2) labelled, resulting from the accurately quantified tag) measured in the mass spectrometry experiment.

Preferably, for the assay peptides with between 8 and 24 amino acids are selected.

The proposed strategy for quantification therefore cleverly makes use of an internal standard which can be universally used for many if not all peptides and makes use of indirect quantification of the peptides of interest which is possible as this internal standard can be attached to the peptide of interest and subsequently released in a stoichiometric amount.

Low-cost synthetic (or recombinantly derived) peptides are thus applied for the first time to the development of high-throughput quantitative proteomics assays. Unpurified synthetic peptides (crude, directly from peptide synthesis (or present in a low complexity digestion mixture)), have been considered so far of limited use in proteomics approaches, due to the unpredictable complexity of their preparations and the lack of accurate quantitation. The gist of this aspect of the invention thus is the coupling of low-budget unpurified synthetic peptides to (1) a mass spectrometry technique that allows to selectively measure target peptides even in complex mixtures, without the need to purify them and (2) to a quantitation strategy that relieves from the typical requirement of using highly purified, accurately quantified labeled peptide standards, of prohibitive cost.

Some advantages of the aspect include:

1. Low-budget: with the current technologies—e.g. the spot-synthesis technology—, it is possible to generate libraries of crude peptides at dramatically lower cost, compared to classical peptide synthesis of highly pure, accurately quantified peptides. This relieves from cost constraints and allows to drastically expand the cost-effective synthesis of target peptides to ideally quantify a whole proteome of interest. Additionally, the quantitation strategy, based on a common tag for all peptides of interest, allows the absolute quantitation of a whole proteome (thousands of proteins) ideally using only one accurately quantified heavy labeled peptide.
2. Speed: Crude peptide libraries can be at present generated at extremely high rate (>50,000 peptides/month). Additionally, the strategy for absolute quantitation can be coupled to MALDI-mass spectrometry, allowing the absolute quantitation of 1,000 peptides in <3 hours.
3. High-throughput: The present invention allows to develop and use SRM assays at dramatically high throughput. The use of crude peptides mixtures to extract the final coordinates of an SRM assay permits to establish and validate hundreds of SRM assays in one single analysis (~1 hour). Once an SRM assay is validated it becomes of universal use and validation/optimization will no longer be necessary prior to analysis. Additionally, upon validation elution times can be extracted to be used as a constraint for further experiments. This is an extremely powerful information, as the use of time-constrained SRM relieves from typical SRM cycle-time restrains, and allows to quantitatively monitor simultaneously a much higher number of SRM assays (>1,000) in one analysis.

Applications:

The presented invention supports the use of SRM as a novel platform for high-throughput quantitative proteomics. For the first time it allows to exploit the drastically higher sensitivity and specificity of SRM for the analysis of thousands of proteins in a reasonable amount of time, making the high-throughput, quantitative analysis of an entire proteome a concrete possibility. This opens possibilities in biotechnological, biomedical, pharmaceutical and biological applications, offering the unique possibility to measure large numbers of target proteins of interest in complex mixtures at high speed and at high quantitative accuracy. The approach is applicable to the analysis of proteins from all organisms, from cells, organs, body fluids, and in the context of both in vivo or in vitro analyses. It also applies to quantitatively monitor post-translational modifications of proteins (e.g. protein phosphorylation, acetylation, methylation), when the corresponding modified peptide can be synthesized/generated. Examples of applications of the invention include the development/use/commercialization of rapid quantitative assays for sets of proteins of interest in the context of pharmaceutical industry (e.g. in the process of development/assay of drugs and analysis of their mechanism of action), biotechnological industry (e.g. design/quality control/assay of recombinant protein preparations), clinical applications (e.g. comparison of healthy vs diseased proteomes to identify biomarkers of disease and their following quantitative analysis for diagnostic, prognostic or therapeutic purposes).

Concrete assays have been determined for a set of human kinases based on experiments with several thousand synthetic peptides. For these proteins peptides were selected according to the invention based on the ionisation potential in a mass spectrometer in a digest of recombinantly expressed kinase proteins. For all selected peptides assays were developed to decide which fragment ions (transitions) are best suited for quantification. In addition to that the retention time in a chromatographic system was determined allowing for prediction of the retention time in any other system based on normalization to a set of reference peptides (SeqID 180-187, see table 2).

In each case a peptide sequence is given which is suitable to measure a protein, i.e. which
- is uniquely contained in the protein of interest (can be determined in silico)
- has a good ionisation property (determined in vitro by measuring a digest of a given protein. A protein on average gives rise to 34 tryptic peptides between 5 and 40 amino-acids (calculated from all human proteins in Uniprot/Swissprot). If they are ranked according to their intensity in a mass spectrometer one usually finds that a small proportion (the highfliers) are much more intense than the others. Knowing these peptides the sensitivity can be boosted by an order of magnitude compared with random selection of peptides.

In addition to that the coordinates for measurement in SRM experiments are determined:
- retention time in a chromatographic system (LC), normalised to a set of standard peptides
- precursor mass (Q1) for the best discharge state (i.e. the most intense charge form)
- the best 5 transitions (Q3) that arise after fragmentation and can be assigned to common b- or y-ions.

The correspondingly determined assays solve the following technical problems:
- which peptide of the human kinases to measure for maximal sensitivity and specificity, this is an intrinsic property of the peptide over different mass spectrometry platforms. Knowing these peptides guarantees high sensitivity.
- Verification of measured signals based on a comparison with determined spectra.

So far, according to the state-of-the-art SRM assays were determined based on evidence from public mass spectrometry data sets (e.g. peptide-Atlas.org) with the help of heavy labelled peptides in purified form. These databases however contain only limited information on which peptide is optimal for a given kinase, nor is it possible to derive the transitions. Furthermore there is so far no set of SRM assays published that would allow a researcher to set up an SRM experiment for measuring these human kinases.

Experimental Part:

Generation of a peptide library—For a set of 61 protein kinases proteotypic peptides (PTPs) were selected according to the following criteria: Only fully tryptic peptides, with no missed cleavages and unique to each protein with evidence from mass spectrometric experiments with recombinantly expressed kinases were considered. Furthermore peptides were constrained to a length between 8 and 24 amino acids. Peptides were synthesized on a micro-scale in an unpurified form using the SPOT-synthesis technology and lyophilized in a 96-well plate (~50 nmol of each peptide/well, JPT Peptide Technology, Berlin, Germany). Peptides were resuspended in 20% acetonitrile, 1% formic acid, vortexed for 30 minutes and sonicated for 15 minutes in the 96-well plate. Aliquots of each peptide contained in a well were mixed (1 pool per plate), evaporated on a vacuum centrifuge to dryness, resolubilized in 0.1% formic acid and immediately analyzed.

Development of SRM assays. For each peptide one precursor/fragment ion transition was calculated for each of the two main charge states (doubly and triply charged), corresponding to the first fragment ion of the y-series with m/z greater than $[m/z_{precursor}+20\ Th]$. The precursor/fragment ion transitions were used to detect by SRM the peptides of interest in the peptide mixtures and to trigger acquisition of the corresponding full fragment ion spectra. In detail, peptide samples were analyzed on a hybrid triple quadrupole/ion trap mass spectrometer (4000QTrap, ABI/MDS-Sciex, Toronto) equipped with a nanoelectrospray ion source. Chromatographic separations of peptides were performed on a Tempo nano LC system (Applied Biosystems) coupled to a 15 cm fused silica emitter, 75 µm diameter, packed with a Magic C18 AQ 5 µm resin (Michrom BioResources, Auburn, Calif., USA). Peptides were loaded on the column from a cooled (4° C.) Tempo auto-sampler and separated with a linear gradient of acetonitrile/water, containing 0.1% formic acid, at a flow rate of 300 nl/min. A gradient from 5 to 30% acetonitrile in 30 or 45 minutes was used. The mass spectrometer was operated in multiple reaction monitoring mode, triggering acquisition of a full MS2 spectrum upon detection of an MRM trace (threshold 300 ion counts). MRM acquisition was performed with Q1 and Q3 operated at unit resolution (0.7 m/z half maximum peak width) with 200 or 300 transitions (dwell-time 10 or 7 ms/transition, respectively) per run. MS2 spectra were acquired in enhanced product ion (EPI) mode for the two highest MRM transitions, using dynamic fill time, Q1 resolution low, scan speed 4000 amu/s, m/z range 300-1400, 2 scans summed. Collision energies used for both MRM and MS2 analyses were calculated according to the formulas: CE=0.044*m/z+5.5 and CE=0.051*m/z+0.55 (CE, collision energy, m/z, mass-to-charge ratio of the precursor ion) for doubly and triply charge precursor ions, respectively.

Fragment ion spectra collected in the QQQ MS were used to validate peptide identities and to extract optimal fragment ions for SRM analysis. MS2 data were searched with Mascot (MatrixScience, Boston, Mass.) against a sub-set of the Uniprot/Swissprot protein database. The database consisted of sequences of all human kinases. A decoy database was generated from this sub-set by reverting amino acid sequences in between tryptic cleavage sites, and appended to the target database. Precursor mass tolerance was set to 2.0 Da and fragment mass tolerance to 1.0 Da. Data were searched allowing only fully tryptic termini, and no missed cleavages. The search results were validated and assigned probabilities using a cut-off for the Mascot ion score where the cut-off was defined by the proportion of assignments to decoy peptides.

Spectral library creation—A spectral library was created from the spectrum-peptide matches. The spectrum with the highest ion score was selected in cases where several spectra matched to a peptide. If more than one charge state was detected the highest scoring spectrum for both charge states were selected. These fragment ion spectra were used as a reference to derive the optimal coordinates of each SRM assay (e.g. best responding fragments, fragment relative intensities, peptide elution time). For each spectrum, the 5 most intense peaks were selected as optimal SRM transitions. Fragments due to neutral loss from precursor were excluded. Fragments with m/z values close to the precursor ion m/z ($|m/z_{Q1}-m/z_{Q3}|\leq 5$ Th) were discarded, as such transitions result in high noise levels. Collision energies associated to each transition were derived from the formulas given above.

The table given below is a list of peptides together with their sequence identification (SeqID) for the sequence listing and the corresponding shortened protein names for which the peptides are characteristic are named as defined according to the UniProt Consortium (www.uniprot.org), which is comprised of the European Bioinformatics Institute (EBI), the Swiss Institute of Bioinformatics (SIB), and the Protein Information Resource (PIR). The corresponding ioncodes for each peptide, the normalized retention times and the relative intensities of the fragments are also given, so each line essentially comprises an assay for SRM determination.

TABLE 1 provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| ABL2 | 4 | NCLVGENHVVK | 2 | y7_1, y8_1, y9_1, b3_1, b4_1 | 100, 84, 58, 31, 12 | 17.1 |
| ABL2 | 4 | NCLVGENHVVK | 3 | y7_1, y8_2, y7_2, y9_2, y5_1 | 100, 94, 41, 21, 20 | 17.1 |
| ABL2 | 5 | WTAPESLAYNTFSIK | 2 | y12_1, y12_2, y8_1, y13_2, y10_1 | 100, 69, 62, 42, 37 | 35 |
| AKT2 | 6 | CGSPSDSSTTEEMEVAVSK | 3 | y4_1, y6_1, y17_2, y10_1, y7_1 | 100, 84, 71, 24, 18 | 23.5 |
| AKT2 | 7 | LGGGPSDAK | 2 | y8_1, y7_1, y5_1, y6_1, | 100, 52, 5, 3 | 3.3 |
| AKT2 | 8 | SDGSFIGYK | 2 | y7_1, y5_1, y8_1, y6_1, | 100, 21, 10, 3 | 21.6 |
| AKT2 | 9 | YDSLGLLELDQR | 2 | y8_1, y6_1, y5_1, y4_1, y10_1 | 100, 83, 55, 24, 21 | 34.2 |
| AKT2 | 9 | YDSLGLLELDQR | 3 | y5_1, y4_1, y3_1, y6_1, b6_1 | 100, 83, 57, 23, 20 | 34.2 |
| BMR1A | 10 | DLEQDEAFIPVGESLK | 2 | y7_1, y8_1, y9_1, b7_1, y5_1 | 100, 41, 33, 15, 14 | 33.2 |
| BMR1A | 11 | NGSCCIADLGLAVK | 2 | y8_1, y9_1, y5_1, y6_1, y7_1 | 100, 56, 48, 44, 25 | 32.3 |
| BMR1A | 12 | SENGVTLAPEDTLPFLK | 2 | y9_1, y4_1, y10_1, y12_1, y11_1 | 100, 44, 40, 33, 13 | 36.9 |
| BMR1A | 12 | SENGVTLAPEDTLPFLK | 3 | y9_2, y4_1, y9_1, y7_1, y10_2 | 100, 69, 62, 54, 21 | 36.9 |
| BMR1A | 13 | YEGSDFQCK | 2 | y7_1, y4_1, y5_1, y6_1, y3_1 | 100, 12, 7, 5, 1 | 16 |
| BMR1B | 14 | LMTECWAHNPASR | 2 | y5_1, y4_1, y6_1, y11_2, y7_1 | 100, 49, 45, 24, 19 | 22.7 |
| BMR1B | 14 | LMTECWAHNPASR | 3 | y4_1, y11_2, y12_2, y6_1, y5_1 | 100, 57, 56, 43, 38 | 22.7 |
| BMR1B | 15 | NGTCCIADLGLAVK | 2 | y8_1, y11_1, y10_1, y7_1, y9_1 | 100, 58, 31, 23, 18 | 30.2 |
| BRD4 | 16 | DAQEFGADVR | 2 | y6_1, y5_1, y7_1, y8_1, b4_1 | 100, 66, 59, 25, 12 | 19.8 |
| BRD4 | 17 | DVPDSQQHPAPEK | 2 | y11_2, y5_1, y9_2, y11_1, y12_2 | 100, 29, 15, 14, 8 | 10.1 |
| BRD4 | 17 | DVPDSQQHPAPEK | 3 | y11_2, y5_1, y10_2, y9_2, y6_1 | 100, 58, 25, 22, 10 | 10.1 |
| BRSK1 | 18 | GGGAGEQPPPPSAR | 2 | y7_1, b7_1, y6_1, y4_1, y5_1 | 100, 18, 15, 7, 6 | 13.4 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| BRSK1 | 19 | SPVFSFSPEPGAGDEAR | 2 | y10_1, y8_1, y11_1, y12_1, y10_2 | 100, 68, 59, 15, 14 | 30.2 |
| BRSK1 | 20 | SVSGASTGLSSSPLSSPR | 2 | y9_1, y12_1, y11_1, y6_1, y13_1 | 100, 65, 44, 40, 16 | 23.4 |
| BRSK1 | 21 | YPSCEDQDLPPR | 2 | y4_1, y11_2, b8_1, y6_1, y8_1 | 100, 22, 13, 12, 9 | 19.2 |
| BUB1B | 22 | FYTGNDPLDVWDR | 2 | y7_1, y3_1, y4_1, y5_1, y11_1 | 100, 37, 36, 18, 16 | 34.7 |
| BUB1B | 22 | FYTGNDPLDVWDR | 3 | y5_1, y3_1, y4_1, b6_1, y7_1 | 100, 46, 35, 27, 16 | 34.7 |
| BUB1B | 23 | YISWTEQNYPQGGK | 2 | y5_1, y10_1, y9_1, y7_1, y6_1 | 100, 36, 21, 17, 16 | 24.8 |
| BUB1B | 23 | YISWTEQNYPQGGK | 3 | y5_1, y7_1, y6_1, b8_1, y4_1 | 100, 14, 12, 4, 2 | 24.8 |
| CAMKV | 24 | GEEAAGYAQESQR | 2 | y8_1, y6_1, y3_1, y7_1, y5_1 | 100, 49, 30, 25, 17 | 14.3 |
| CAMKV | 25 | ITAEEAISHEWISGNAASDK | 3 | y18_2, y8_1, y19_2, y15_2, y17_2 | 100, 62, 31, 23, 13 | 29.8 |
| CAMKV | 26 | QVLEAVAYLHSLK | 2 | y7_1, y11_1, y10_1, y6_1, y4_1 | 100, 71, 61, 57, 56 | 32.3 |
| CAMKV | 26 | QVLEAVAYLHSLK | 3 | y7_1, y5_1, y6_1, y7_2, y11_2 | 100, 60, 58, 38, 32 | 32.3 |
| CAMKV | 27 | TEEFCEIFR | 2 | y7_1, y6_1, y5_1, y4_1, y3_1 | 100, 58, 27, 18, 5 | 31.3 |
| CDK4 | 28 | APPPGLPAETIK | 2 | y10_1, y10_2, y11_2, y9_1, y5_1 | 100, 86, 41, 36, 19 | 23 |
| CDK4 | 29 | DLKPENILVTSGGTVK | 2 | y13_1, y15_2, y9_1, y8_1, y14_2 | 100, 33, 17, 11, 7 | 25.5 |
| CDK4 | 30 | YEPVAEIGVGAYGTVYK | 2 | y10_1, y15_2, y8_1, y13_1, y12_1 | 100, 76, 69, 53, 39 | 30.3 |
| CDK4 | 30 | YEPVAEIGVGAYGTVYK | 3 | y8_1, y6_1, y5_1, b6_1, y7_1 | 100, 28, 27, 16, 13 | 30.3 |
| CDK6 | 31 | ADQQYECVAEIGEGAYGK | 2 | y5_1, y7_1, y8_1, b12_2, y13_1 | 100, 97, 28, 26, 8 | 27 |
| CDK6 | 31 | ADQQYECVAEIGEGAYGK | 3 | y7_1, b8_1, y8_1, y5_1, b5_1 | 100, 28, 26, 21, 10 | 27 |
| CDK6 | 32 | GSSDVDQLGK | 2 | y5_1, y6_1, y8_1, y7_1, y4_1 | 100, 87, 68, 48, 26 | 14.7 |
| CDK6 | 33 | HLETFEHPNVVR | 3 | y5_1, b6_1, y11_2, y10_2, b7_2 | 100, 37, 25, 23, 16 | 7.6 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| CDK6 | 34 | ISAYSALSHPYFQDLER | 2 | y8_1, y3_1, y10_1, b9_1, b6_1 | 100, 24, 19, 14, 7 | 32.1 |
| CDK6 | 34 | ISAYSALSHPYFQDLER | 3 | y16_2, y8_1, y15_2, y14_2, y3_1 | 100, 76, 55, 44, 37 | 32.1 |
| CDK8 | 35 | EFLTEEEPDDK | 2 | y8_1, y4_1, y6_1, y7_1, b10_2 | 100, 94, 42, 41, 24 | 21.7 |
| CDK8 | 36 | MPEHSTLMK | 2 | y8_2, y8_1, y6_1, y7_1, y5_1 | 100, 41, 24, 18, 16 | 15.6 |
| CDK8 | 36 | MPEHSTLMK | 3 | y8_2, y6_1, y5_1, b7_1, y7_2 | 100, 30, 15, 4, 3 | 15.6 |
| CDK8 | 37 | TSNPYHHDQLDR | 2 | y4_1, y9_2, y6_1, y5_1, b8_1 | 100, 87, 70, 69, 38 | 14.1 |
| CDK8 | 37 | TSNPYHHDQLDR | 3 | y9_2, y10_2, y7_2, y4_1, y6_1 | 100, 39, 27, 17, 14 | 14.1 |
| CDKL2 | 38 | HENLVNLLEVCK | 3 | b6_1, y5_1, y3_1, y4_1, b5_1 | 100, 83, 43, 38, 28 | 31.2 |
| CDKL2 | 39 | TLAAPGEVYTDYVATR | 2 | y12_1, y12_2, y8_1, y10_2, y13_2 | 100, 72, 30, 27, 23 | 29.9 |
| CDKL2 | 40 | YENLGLVGEGSYGMVMK | 2 | y10_1, y11_1, y8_1, y13_1, b3_1 | 100, 42, 26, 20, 15 | 32.5 |
| CHK2 | 41 | RPLNNNSEIALSLSR | 3 | y4_1, y6_1, y5_1, b8_1, y7_1 | 100, 78, 63, 51, 45 | 24.5 |
| CHK2 | 42 | TLGSGACGEVK | 2 | y9_1, y7_1, y8_1, y5_1, y9_2 | 100, 19, 18, 13, 8 | 14.9 |
| CHK2 | 43 | YNFIPEVWAEVSEK | 2 | y10_1, b3_1, y9_2, y10_2, y11_1 | 100, 56, 10, 8, 5 | 39.8 |
| CHK2 | 43 | YNFIPEVWAEVSEK | 3 | y6_1, y7_1, y5_1, b3_1, y9_2 | 100, 89, 66, 54, 37 | 39.8 |
| DAPK3 | 44 | ESLTEDEATQFLK | 2 | y8_1, y10_1, y9_1, y6_1, y5_1 | 100, 77, 71, 52, 46 | 29.2 |
| DAPK3 | 45 | LCHEDVEALAAIYEEK | 2 | y4_1, y6_1, y7_1, y10_1, y14_2 | 100, 99, 79, 73, 52 | 30.8 |
| DAPK3 | 45 | LCHEDVEALAAIYEEK | 3 | y7_1, y6_1, b8_1, y5_1, y4_1 | 100, 87, 70, 62, 52 | 30.8 |
| DAPK3 | 46 | VLEEAAAEEGLR | 2 | y7_1, y8_1, y11_1, y9_1, y10_1 | 100, 72, 42, 37, 27 | 25 |
| DAPK3 | 46 | VLEEAAAEEGLR | 3 | y6_1, y4_1, y5_1, b6_1, y7_1 | 100, 66, 42, 15, 14 | 25 |
| DCLK1 | 47 | GGDLFDAITSTNK | 2 | y9_1, y8_1, y5_1, y7_1, y4_1 | 100, 99, 39, 37, 16 | 30.7 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| DCLK1 | 48 | ISSLDQLVEGESYVCGSIEPFK | 2 | y3_1, y4_1, y11_1, y8_1, y7_1 | 100, 87, 83, 64, 61 | 39.1 |
| DCLK1 | 48 | ISSLDQLVEGESYVCGSIEPFK | 3 | y8_1, y7_1, y3_1, y4_1, y9_1 | 100, 62, 44, 22, 19 | 39.1 |
| DCLK1 | 49 | SFEALLADLTR | 2 | y6_1, y5_1, y7_1, y8_1, y9_1 | 100, 88, 62, 59, 45 | 42.1 |
| DCLK1 | 50 | YQDDFLLDESECR | 2 | y6_1, y7_1, y8_1, y4_1, b4_1 | 100, 70, 55, 38, 23 | 30.6 |
| DCLK1 | 50 | YQDDFLLDESECR | 3 | y6_1, y4_1, b6_1, y5_1, b5_1 | 100, 58, 32, 29, 16 | 30.6 |
| EGFR | 51 | EISDGDVIISGNK | 2 | y11_1, y6_1, y4_1, y5_1, y7_1 | 100, 39, 37, 32, 29 | 22.3 |
| EGFR | 51 | EISDGDVIISGNK | 3 | y5_1, y4_1, y6_1, b7_1, y11_2 | 100, 87, 36, 15, 8 | 22.3 |
| EGFR | 52 | VCNGIGIGEFK | 2 | y9_1, y6_1, y4_1, y8_1, y10_2 | 100, 80, 60, 56, 32 | 26.9 |
| EGFR | 52 | VCNGIGIGEFK | 3 | y4_1, y6_1, b4_1, y5_1, b6_1 | 100, 50, 17, 13, 3 | 26.9 |
| EPHA3 | 53 | DCNSIPLVLGTCK | 2 | y8_1, b4_1, y5_1, y4_1, y6_1 | 100, 12, 9, 6, 4 | 29.6 |
| EPHA3 | 53 | DCNSIPLVLGTCK | 3 | y5_1, y4_1, y8_1, y6_1, b5_1 | 100, 89, 83, 66, 24 | 29.6 |
| EPHA3 | 54 | FEQIVSILDK | 2 | y6_1, y8_1, y5_1, y7_1, y4_1 | 100, 74, 69, 67, 13 | 32.4 |
| EPHA3 | 55 | VVGAGEFGEVCSGR | 2 | y8_1, y7_1, y10_1, y12_1, y4_1 | 100, 91, 77, 60, 46 | 24 |
| EPHA3 | 55 | VVGAGEFGEVCSGR | 3 | y5_1, y7_1, y8_1, b6_1, y6_1 | 100, 66, 23, 20, 18 | 24 |
| EPHA7 | 56 | FEQIVGILDK | 2 | y6_1, y5_1, y8_1, y7_1, b4_1 | 100, 97, 77, 66, 18 | 31.2 |
| EPHA7 | 57 | GTCVSSAEEEAENAPR | 2 | y8_1, y12_1, y11_1, y8_2, y6_1 | 100, 64, 57, 35, 28 | 9.6 |
| EPHA7 | 57 | GTCVSSAEEEAENAPR | 3 | y4_1, y5_1, y6_1, y8_2, y7_1 | 100, 69, 52, 43, 16 | 9.6 |
| EPHA7 | 58 | LDVATLEEATGK | 2 | y8_1, y9_1, y7_1, y6_1, b5_1 | 100, 88, 42, 37, 28 | 27.4 |
| EPHA8 | 59 | DCNSMPGVLGTCK | 2 | y8_1, y5_1, y9_1, y4_1, y11_1 | 100, 13, 10, 9, 8 | 23.8 |
| EPHA8 | 60 | MYCSAEGEWLVPIGK | 2 | y4_1, b6_1, y5_1, y7_1, y7_1 | 100, 4, 3, 2 | 34.5 |
| EPHAA | 61 | EALLSGISALQAR | 2 | y9_1, y8_1, y5_1, y10_1, y7_1 | 100, 53, 21, 17, 9 | 32.9 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| FGFR1 | 62 | CPSSGTPNPTLR | 2 | y6_1, y8_1, y4_1, y9_1, b6_1 | 100, 24, 22, 20, 15 | 16.6 |
| FGFR1 | 63 | IGPDNLPYVQILK | 2 | y7_1, y11_2, y12_2, y8_1, b5_1 | 100, 87, 23, 16, 13 | 34.2 |
| FGFR1 | 63 | IGPDNLPYVQILK | 3 | y5_1, y7_1, y7_2, y6_1, y4_1 | 100, 95, 57, 56, 32 | 34.2 |
| FGFR1 | 64 | TVALGSNVEFMCK | 2 | y9_1, y11_1, y5_1, y10_1, y11_2 | 100, 17, 14, 9, 7 | 28.8 |
| FGFR2 | 65 | DLVSCTYQLAR | 2 | y8_1, y7_1, y5_1, y6_1, y9_1 | 100, 14, 10, 8, 5 | 29.4 |
| FGFR2 | 65 | DLVSCTYQLAR | 3 | y4_1, y5_1, y6_1, y7_1, y7_2 | 100, 22, 14, 5, 3 | 29.4 |
| FGFR2 | 66 | LTLGKPLGEGCFGQVVMAEAVGIDK | 3 | y18_2, y10_1, y8_1, y6_1, y5_1 | 100, 40, 22, 14, 11 | 37.8 |
| FGFR4 | 67 | DLADLVSEMEVMK | 2 | y7_1, y8_1, b5_1, y10_1, b4_1 | 100, 77, 38, 37, 26 | 41.8 |
| FGFR4 | 68 | RPPGPDLSPDGPR | 3 | y5_1, y4_1, b8_2, b6_1, b8_1 | 100, 15, 12, 10, 8 | 18.9 |
| FGFR4 | 69 | VLLAVSEEYLDLR | 2 | y8_1, y9_1, y11_1, y10_1, y5_1 | 100, 46, 24, 20, 15 | 36.5 |
| FLT3 | 70 | HSSLNCQPHFDLQNR | 2 | y4_1, y8_1, y6_1, y8_2, b7_1 | 100, 44, 9, 7, 6 | 21.8 |
| FLT3 | 70 | HSSLNCQPHFDLQNR | 3 | y4_1, y8_1, y6_1, y14_2, b9_2 | 100, 68, 60, 52, 41 | 21.8 |
| FRAP | 71 | GGILAIASLIGVEGGNATR | 2 | y9_1, y10_1, y8_1, y12_1, y7_1 | 100, 80, 60, 35, 29 | 41.9 |
| FYN | 72 | DGSLNQSSGYR | 2 | y5_1, y7_1, y6_1, y4_1, b8_2 | 100, 59, 53, 43, 16 | 15.5 |
| FYN | 73 | QLLSFGNPR | 2 | y6_1, y7_1, y5_1, y4_1, y8_1 | 100, 81, 56, 55, 5 | 27.3 |
| FYN | 74 | TLKPGTMSPESFLEEAQIMK | 3 | y5_1, b4_1, y8_1, y3_1, y7_1 | 100, 85, 67, 28, 26 | 37.9 |
| IKKA | 75 | CIFACEEMSGEVR | 2 | y10_1, b3_1, y9_1, y11_1, y4_1 | 100, 62, 50, 49, 25 | 28.1 |
| IKKA | 76 | DLKPENIVLQDVGGK | 2 | y12_1, y14_2, y13_2, y7_1, y12_2 | 100, 25, 18, 15, 9 | 28.5 |
| IKKA | 76 | DLKPENIVLQDVGGK | 3 | y7_1, b6_1, b7_1, y6_1, y8_1 | 100, 55, 50, 32, 29 | 28.5 |
| IKKA | 77 | SLSDCVNYIVQDSK | 2 | b10_2, y8_1, y6_1, y7_1, y9_1 | 100, 90, 62, 24, 19 | 29.5 |
| IKKA | 77 | SLSDCVNYIVQDSK | 3 | y5_1, y8_1, y7_1, b8_1, b5_1 | 100, 21, 16, 10, 7 | 29.5 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| IKKA | 78 | TVYEGPFASR | 2 | y8_1, y6_1, y7_1, y5_1, y8_2 | 100, 74, 28, 10, 3 | 25 |
| IRAK1 | 79 | DLVEEEAEEAGVALR | 2 | b11_2, y9_1, y5_1, b6_1, y8_1 | 100, 69, 54, 46, 44 | 33.3 |
| IRAK1 | 79 | DLVEEEAEEAGVALR | 3 | y5_1, b11_2, b6_1, b8_2, y8_1 | 100, 70, 49, 12, 10 | 33.3 |
| IRAK1 | 80 | GTLAYLPEEYIK | 2 | y6_1, y7_1, y8_1, y9_1, b9_2 | 100, 59, 51, 35, 14 | 32.2 |
| ITK | 81 | AVVSENNPCIK | 2 | y6_1, y7_1, y4_1, y8_1, y9_1 | 100, 62, 48, 31, 27 | 17.1 |
| ITK | 81 | AVVSENNPCIK | 3 | y4_1, y5_1, y6_1, y7_1, b6_1 | 100, 10, 6, 4, 2 | 17.1 |
| ITK | 82 | EGAMSEEDFIEEAEVMMK | 2 | y9_1, y3_1, y4_1, y8_1, y11_1 | 100, 73, 54, 53, 38 | 41.3 |
| ITK | 82 | EGAMSEEDFIEEAEVMMK | 3 | y8_1, y3_1, y6_1, b9_1, y9_2 | 100, 29, 21, 18, 16 | 41.3 |
| ITK | 83 | NCLVGENQVIK | 2 | y7_1, y8_1, b4_1, b3_1, y9_1 | 100, 31, 20, 12, 6 | 23.4 |
| ITK | 83 | NCLVGENQVIK | 3 | b3_1, b4_1, y5_1, b5_1, y7_1 | 100, 97, 64, 20, 16 | 23.4 |
| ITK | 84 | SPNNLETYEWYNK | 2 | y4_1, y7_1, y8_1, y3_1, y5_1 | 100, 46, 40, 35, 33 | 27.3 |
| ITK | 84 | SPNNLETYEWYNK | 3 | y5_1, y4_1, y3_1, b5_1, b7_1 | 100, 76, 47, 23, 11 | 27.3 |
| KPSH2 | 85 | TLCGTPEYIAPEVLLR | 2 | y7_1, y11_1, y6_1, y9_1, y4_1 | 100, 87, 45, 20, 9 | 35.6 |
| KS6A2 | 86 | DESGSPESIR | 2 | y8_1, y5_1, y7_1, y6_1, y9_2 | 100, 58, 39, 4, 3 | 14.7 |
| KS6A2 | 87 | EASDVLCTITK | 2 | y6_1, y9_1, y4_1, y8_1, y7_1 | 100, 18, 14, 10, 8 | 26.3 |
| KS6A2 | 88 | LGMPQFLSGEAQSLLR | 2 | y9_1, y13_2, y10_1, y11_1, y6_1 | 100, 98, 35, 30, 26 | 41.1 |
| KS6A2 | 88 | LGMPQFLSGEAQSLLR | 3 | y4_1, y6_1, y5_1, y7_1, y3_1 | 100, 53, 40, 17, 11 | 41.1 |
| KSR2 | 89 | EAPPCHLLIIHR | 3 | y4_1, y9_2, y10_2, y3_1, y5_1 | 100, 93, 50, 42, 41 | 24 |
| KSYK | 90 | EEAEDYLVQGGMSDGLYLLR | 2 | y6_1, y11_1, y7_1, y4_1, y12_1 | 100, 76, 25, 22, 16 | 38.2 |
| KSYK | 90 | EEAEDYLVQGGMSDGLYLLR | 3 | y8_1, y7_1, y6_1, y11_1, y17_2 | 100, 99, 90, 59, 39 | 38.2 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---------|-------|-----|--------|----------|----------------|----------------|
| KSYK | 91 | NYLGGFALSVAHGR | 2 | y11_1, y8_1, y6_1, y12_2, y10_1 | 100, 58, 47, 41, 38 | 28.2 |
| KSYK | 92 | QTWNLQGQALEQAIISQKPQLEK | 3 | y5_1, b8_1, y9_1, y21_2, y19_2 | 100, 46, 43, 22, 13 | 33.8 |
| KSYK | 93 | YLEESNFVHR | 2 | y8_1, y6_1, y7_1, y9_2, y3_1 | 100, 92, 55, 19, 15 | 20.9 |
| KSYK | 93 | YLEESNFVHR | 3 | y4_1, y6_1, y5_1, y8_2, b8_2 | 100, 63, 53, 44, 41 | 20.9 |
| LCK | 94 | AANILVSDTLSCK | 2 | y8_1, y7_1, y5_1, y3_1, y9_1 | 100, 65, 29, 18, 17 | 28.3 |
| LCK | 94 | AANILVSDTLSCK | 3 | y3_1, y5_1, y7_1, y4_1, b5_1 | 100, 94, 52, 50, 30 | 28.3 |
| LCK | 95 | ESESTAGSFSLSVR | 2 | y9_1, y8_1, y10_1, y5_1, y6_1 | 100, 94, 31, 28, 23 | 26.5 |
| LCK | 96 | HYTNASDGLCTR | 2 | y5_1, y10_1, y9_1, y11_1, b3_1 | 100, 85, 27, 18, 15 | 14.9 |
| LCK | 96 | HYTNASDGLCTR | 3 | b5_1, y6_1, y3_1, y5_1, b4_1 | 100, 75, 68, 63, 60 | 14.9 |
| MAPK3 | 98 | LGQYGFPNPEWSEVSEDAK | 2 | b6_1, y5_1, y4_1, y8_1, y11_1 | 100, 59, 33, 31, 28 | 32.5 |
| MAPK3 | 99 | QVLGLGVNGK | 2 | y8_1, y7_1, y6_1, y4_1, y9_1 | 100, 80, 24, 4, 1 | 22.8 |
| MAPK3 | 99 | QVLGLGVNGK | 3 | y5_1, b4_1, b6_1, y6_1, | 100, 15, 12, 6 | 22.8 |
| MET | 100 | GDLTIANLGTSEGR | 2 | y6_1, y9_1, y8_1, y7_1, y4_1 | 100, 62, 56, 43, 24 | 25 |
| MET | 101 | ITDIGEVSQFLTEGIIMK | 2 | y5_1, y11_1, y4_1, y9_1, b7_1 | 100, 63, 53, 34, 31 | 37.9 |
| MET | 102 | VFPNSAPLEGGTR | 2 | y11_2, y7_1, y11_1, y8_1, y10_1 | 100, 77, 17, 16, 5 | 23.9 |
| MK08 | 103 | LFPDVLFPADSEHNK | 2 | y8_1, y13_2, y9_1, y5_1, b5_1 | 100, 39, 35, 19, 16 | 33.6 |
| MK08 | 103 | LFPDVLFPADSEHNK | 3 | y8_1, y9_1, y5_1, y13_2, y8_2 | 100, 29, 28, 23, 20 | 33.6 |
| MK08 | 104 | NIIGLLNVFTPQK | 2 | y10_1, y11_1, y8_1, y7_1, y5_1 | 100, 72, 48, 43, 40 | 41.8 |
| MK08 | 105 | YAGYSFEK | 2 | y6_1, y7_1, y4_1, y5_1, y3_1 | 100, 57, 16, 8, 5 | 20.8 |
| MK09 | 106 | GCVIFQGTDHIDQWNK | 3 | b14_2, y13_2, y12_2, y4_1, b9_2 | 100, 66, 54, 29, 22 | 28.3 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| MK09 | 107 | ISVDEALR | 2 | y7_1, y6_1, y5_1, y4_1, | 100, 80, 76, 31 | 23.7 |
| MK09 | 108 | VIEQLGTPSAEFMK | 2 | y9_1, y7_1, y10_1, b4_1, y3_1 | 100, 76, 29, 21, 11 | 28.6 |
| MK14 | 109 | DLKPSNLAVNEDCELK | 2 | y15_2, y4_1, y7_1, y5_1, y14_2 | 100, 46, 36, 27, 18 | 24.3 |
| MK14 | 109 | DLKPSNLAVNEDCELK | 3 | y7_1, b6_1, y8_1, b7_1, b8_1 | 100, 77, 56, 47, 46 | 24.3 |
| MK14 | 110 | HENVIGLLDVFTPAR | 3 | y5_1, y12_2, b7_1, y7_1, b9_1 | 100, 56, 53, 46, 39 | 39.4 |
| MK14 | 111 | YIHSADIIHR | 2 | y8_1, y8_2, y7_1, y6_1, y4_1 | 100, 71, 42, 28, 21 | 19.1 |
| MK14 | 111 | YIHSADIIHR | 3 | y3_1, y8_2, y7_1, b6_1, y5_1 | 100, 47, 27, 21, 13 | 19.1 |
| MK14 | 112 | YQNLSPVGSGAYGSVCAAFDTK | 3 | y10_1, y7_1, y5_1, y6_1, b4_1 | 100, 68, 59, 44, 29 | 31.5 |
| MP2K7 | 113 | SAGCAAYMAPER | 2 | y6_1, y5_1, y7_1, y8_1, y3_1 | 100, 63, 56, 44, 31 | 18.8 |
| MP2K7 | 113 | SAGCAAYMAPER | 3 | y4_1, y3_1, y5_1, b7_1, y6_1 | 100, 69, 54, 35, 21 | 18.8 |
| MP2K7 | 114 | YETLEVDVASWFK | 2 | y9_1, y7_1, y4_1, y10_1, y11_1 | 100, 80, 70, 58, 54 | 41.6 |
| NEK7 | 115 | AACLLDGVPVALK | 2 | y5_1, y9_1, y8_1, y7_1, b8_1 | 100, 47, 41, 33, 12 | 39 |
| NEK7 | 116 | IEQCDYPPLPSDHYSEELR | 3 | y13_2, y7_1, b10_2, y10_2, y12_2 | 100, 40, 32, 29, 15 | 27.4 |
| NEK7 | 117 | TTAAHSLVGTPYYMSPER | 3 | y6_1, y5_1, y4_1, y8_1, y8_2 | 100, 71, 55, 44, 43 | 26.5 |
| NEK7 | 118 | VQIFDLMDAK | 2 | y8_1, y7_1, y4_1, y6_1, y5_1 | 100, 55, 18, 17, 9 | 34.7 |
| NTRK3 | 119 | LNSQNLYCINADGSQLPLFR | 2 | y4_1, y8_1, y11_1, y5_1, y10_1 | 100, 33, 19, 7, 5 | 36.8 |
| NTRK3 | 119 | LNSQNLYCINADGSQLPLFR | 3 | y4_1, y8_1, y5_1, y9_1, b5_1 | 100, 39, 31, 21, 10 | 36.8 |
| NTRK3 | 120 | VFLAECYNLSPTK | 2 | y10_1, y9_1, y8_1, y7_1, y11_1 | 100, 40, 29, 18, 15 | 29.2 |
| NTRK3 | 120 | VFLAECYNLSPTK | 3 | y4_1, y6_1, y12_2, y5_1, b4_1 | 100, 37, 27, 20, 16 | 29.2 |
| NTRK3 | 121 | VVSLEEPELR | 2 | y8_1, y6_1, y4_1, y5_1, y7_1 | 100, 45, 40, 32, 16 | 25.9 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---------|-------|-----|--------|----------|----------------|----------------|
| NTRK3 | 122 | WMQLWQEQGEAK | 2 | y8_1, y9_1, y7_1, b3_1, y6_1 | 100, 57, 39, 36, 35 | 31 |
| NUAK2 | 123 | EPPKPSDACGLIR | 3 | y4_1, y5_1, y7_1, y9_2, y11_2 | 100, 46, 12, 10, 8 | 21.9 |
| NUAK2 | 124 | IVIVMEYASR | 2 | y6_1, y8_1, y7_1, y4_1, y5_1 | 100, 83, 78, 29, 10 | 29.8 |
| NUAK2 | 125 | LENILLDANGNIK | 2 | y9_1, y8_1, y7_1, b4_1, b8_2 | 100, 91, 61, 26, 21 | 30.4 |
| NUAK2 | 125 | LENILLDANGNIK | 3 | y7_1, y5_1, b5_1, y4_1, b8_2 | 100, 61, 50, 44, 22 | 30.4 |
| NUAK2 | 126 | SGPTPSAAELARPLAEGLIK | 3 | y16_2, y17_2, y15_2, y4_1, y18_2 | 100, 14, 13, 5, 4 | 31.8 |
| NUAK2 | 127 | VGEQEAPHEGGHPGSDSAR | 3 | y7_1, y13_2, y12_2, y14_2, y18_2 | 100, 60, 24, 22, 20 | 11.3 |
| PAK7 | 128 | ASSSSPLDYSFQFTPSR | 2 | y9_1, y10_1, y4_1, y8_1, y7_1 | 100, 86, 77, 41, 30 | 33.3 |
| PAK7 | 129 | HGEAYYSEVKPLK | 2 | y12_1, y8_1, b8_1, b6_1, b9_1 | 100, 89, 70, 59, 49 | 18.5 |
| PAK7 | 129 | HGEAYYSEVKPLK | 3 | b5_1, y5_1, y7_1, b6_1, y6_1 | 100, 20, 18, 16, 14 | 18.5 |
| PAK7 | 130 | IGEGSTGIVCIATEK | 2 | y7_1, y9_1, y6_1, y12_1, y10_1 | 100, 73, 63, 37, 36 | 26.2 |
| PAK7 | 130 | IGEGSTGIVCIATEK | 3 | y6_1, y7_1, y5_1, y4_1, b6_1 | 100, 56, 42, 17, 7 | 26.2 |
| PDK3 | 131 | AAPLAGFGYGLPISR | 2 | y13_2, y10_1, y8_1, y11_1, y4_1 | 100, 53, 43, 38, 33 | 34.5 |
| PDK3 | 132 | LYSMEGVGTDAVIYLK | 2 | y11_1, y9_1, y3_1, y4_1, y6_1 | 100, 95, 47, 41, 22 | 34.7 |
| PDK3 | 133 | TTPEADDWSNPSSEPR | 2 | y14_2, y6_1, y8_1, y9_1, y7_1 | 100, 89, 44, 12, 9 | 16.4 |
| PFTK2 | 134 | LPNYNPEWFPLPTPR | 2 | y10_1, y6_1, b5_1, y4_1, y7_1 | 100, 65, 43, 38, 32 | 38.4 |
| PFTK2 | 134 | LPNYNPEWFPLPTPR | 3 | y6_1, y4_1, b7_1, b5_1, b4_1 | 100, 55, 35, 16, 12 | 38.4 |
| PFTK2 | 135 | SLPFGAASSYLNLEK | 2 | y13_2, y11_1, y9_1, y8_1, y7_1 | 100, 32, 25, 17, 9 | 34.8 |
| PFTK2 | 135 | SLPFGAASSYLNLEK | 3 | y5_1, y4_1, y6_1, y7_1, y11_1 | 100, 73, 65, 28, 22 | 34.8 |
| PFTK2 | 136 | SNSDCFQEEDLR | 2 | y10_1, y7_1, y6_1, y3_1, y5_1 | 100, 88, 86, 80, 75 | 20.7 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---------|-------|-----|--------|----------|----------------|----------------|
| PFTK2 | 136 | SNSDCFQEEDLR | 3 | y5_1, b7_2, y3_1, y6_1, b5_1 | 100, 25, 13, 8, 7 | 20.7 |
| PFTK2 | 137 | VISMNAEEGVPFTAIR | 2 | y6_1, y10_1, y11_1, y9_1, y7_1 | 100, 14, 12, 8, 6 | 33 |
| PGFRB | 138 | GGPIYIITEYCR | 2 | y6_1, y7_1, b5_1, y8_1, y4_1 | 100, 87, 58, 28, 24 | 32.6 |
| PGFRB | 139 | GMPQPNIIWSACR | 2 | y9_1, y11_2, y6_1, y5_1, y11_1 | 100, 38, 23, 20, 11 | 31.3 |
| PGFRB | 140 | IMSHLGPHLNVVNLLGACTK | 3 | y5_1, y6_1, b11_2, y8_1, b13_2 | 100, 89, 74, 68, 45 | 32.4 |
| PIM1 | 141 | AAPCNDLHATK | 2 | y9_2, y5_1, y9_1, y7_1, y8_1 | 100, 8, 6, 4, 3 | 11.2 |
| PIM1 | 141 | AAPCNDLHATK | 3 | y9_2, y7_1, y8_2, y8_1, y4_1 | 100, 10, 9, 8, 7 | 11.2 |
| PIM1 | 142 | GALQEELAR | 2 | y5_1, y6_1, y7_2, y7_1, | 100, 93, 23, 9 | 21.3 |
| PIM1 | 143 | VSDNLPVAIK | 2 | y9_1, y8_1, y9_2, y6_1, y7_1 | 100, 87, 50, 31, 24 | 23.4 |
| PLK2 | 144 | HDFFLQGFTPDR | 2 | y10_1, y6_1, y9_1, y8_1, y3_1 | 100, 87, 68, 59, 46 | 32.4 |
| PLK2 | 144 | HDFFLQGFTPDR | 3 | y6_1, b9_2, b5_1, y3_1, y5_1 | 100, 99, 53, 51, 24 | 32.4 |
| PLK2 | 145 | LGNFFINEAMELK | 2 | y7_1, y9_1, y5_1, y10_1, b5_1 | 100, 96, 35, 32, 29 | 38.9 |
| PLK2 | 146 | TDEELQPPTTTVAR | 2 | y8_1, b5_1, y9_1, b6_1, y11_2 | 100, 6, 4, 3, 2 | 22.3 |
| PLK2 | 147 | TICGTPNYLSPEVLNK | 2 | y11_1, y6_1, y4_1, y7_1, y9_1 | 100, 43, 29, 26, 10 | 29.3 |
| ROR1 | 148 | EVVSSTGVLFVK | 2 | y9_1, y10_1, y8_1, y6_1, y7_1 | 100, 68, 46, 28, 17 | 28.3 |
| ROR1 | 149 | NILIGEQLHVK | 2 | y7_1, y9_1, y8_1, y6_1, b4_1 | 100, 53, 43, 11, 9 | 25.2 |
| ROR1 | 149 | NILIGEQLHVK | 3 | y7_1, y8_2, y7_2, y9_2, y5_1 | 100, 38, 20, 17, 8 | 25.2 |
| ROR1 | 150 | VSGNPPPTIR | 2 | y6_1, y5_1, y3_1, y9_1, y8_2 | 100, 31, 5, 4, 3 | 16.3 |
| SG494 | 151 | MENILLDER | 2 | y5_1, y7_1, y4_1, y6_1, y8_1 | 100, 70, 53, 27, 20 | 28.5 |
| SNRK | 152 | CAGPSNSMQLASR | 2 | y11_1, y11_2, y6_1, y7_1, y10_1 | 100, 86, 58, 52, 49 | 18.9 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| SNRK | 153 | DAIVEALETNR | 2 | y8_1, y6_1, y5_1, y7_1, y4_1 | 100, 45, 32, 26, 11 | 28.3 |
| SNRK | 153 | DAIVEALETNR | 3 | y4_1, y3_1, y6_1, b6_1, b10_2 | 100, 68, 23, 10, 5 | 28.3 |
| SNRK | 154 | LDTLATGHLFQEVR | 2 | y9_1, y4_1, y12_2, y3_1, b4_1 | 100, 38, 30, 23, 15 | 30.8 |
| SNRK | 154 | LDTLATGHLFQEVR | 3 | y10_2, y13_2, y6_1, y12_2, y5_1 | 100, 49, 48, 47, 45 | 30.8 |
| SNRK | 155 | MCISSTGNAGQVPAVGGIK | 2 | y7_1, y12_1, y11_1, y5_1, y8_1 | 100, 6, 4, 3, 2 | 25.7 |
| ST32A | 156 | KPPVFDENEDVNFDHFEILR | 3 | y18_2, y5_1, y10_2, y4_1, y7_1 | 100, 84, 75, 53, 46 | 31.8 |
| ST32A | 157 | LLEPNPDQR | 2 | y6_1, y4_1, y7_1, y3_1 | 100, 62, 11, 5 | 17.9 |
| ST32B | 158 | LQDGCNNNLLTHTCTR | 2 | y6_1, y4_1, y5_1, y13_2, y3_1 | 100, 77, 52, 47, 22 | 20.4 |
| ST32B | 158 | LQDGCNNNLLTHTCTR | 3 | y14_2, y6_1, y13_2, y11_2, y4_1 | 100, 66, 50, 40, 28 | 20.4 |
| ST32B | 159 | LYICELALALEYLQR | 2 | y7_1, y8_1, y4_1, y6_1, b10_2 | 100, 84, 71, 64, 63 | 43.5 |
| ST32B | 159 | LYICELALALEYLQR | 3 | y4_1, y5_1, y6_1, y3_1, b7_1 | 100, 58, 44, 40, 18 | 43.5 |
| STK11 | 160 | AVCMNGTEAAQLSTK | 2 | y10_1, y7_1, b5_1, y12_1, y4_1 | 100, 91, 65, 64, 59 | 21.4 |
| STK11 | 160 | AVCMNGTEAAQLSTK | 3 | y6_1, b5_1, y7_1, b7_1, b9_2 | 100, 81, 76, 43, 34 | 21.4 |
| STK11 | 161 | DIKPGNLLLTTGGTLK | 2 | y13_1, y15_2, y14_2, y7_1, y13_2 | 100, 38, 30, 10, 9 | 30.5 |
| STK11 | 161 | DIKPGNLLLTTGGTLK | 3 | y8_1, y7_1, b7_1, y5_1, b6_1 | 100, 72, 51, 46, 44 | 30.5 |
| STK11 | 162 | ISDLGVAEALHPFAADDTCR | 3 | y9_1, y3_1, y14_2, y16_2, y17_2 | 100, 77, 76, 64, 48 | 33.5 |
| STK11 | 163 | NVIQLVDVLYNEEK | 2 | y8_1, y9_1, y5_1, y11_1, y10_1 | 100, 90, 43, 37, 35 | 41.4 |
| STK11 | 163 | NVIQLVDVLYNEEK | 3 | y5_1, y6_1, y8_1, b7_1, y4_1 | 100, 78, 43, 28, 24 | 41.4 |
| STK11 | 164 | YLMGDLLGEGSYGK | 2 | y7_1, y12_1, y11_1, y8_1, y9_1 | 100, 63, 48, 46, 16 | 33.9 |
| STK19 | 165 | ACDGRPYAGAVQK | 3 | y11_2, y10_2, y12_2, y5_1, b11_2 | 100, 47, 24, 3, 2 | 13.6 |

TABLE 1-continued provides SRM assay coordinates to be used for measuring indicated proteins in an SRM experiment. Transitions are selected from a full MS/MS spectrum. Only spectrum peaks that could be assigned either to a fragment from the b or y-ion series (fragment charge state +1 and +2) are indicated. The five most intense peaks are indicated where available. Ion-types are coded as [b|y]position.precursor-charge.fragment-charge. The corresponding relative intensities are shown in the order corresponding to the ion-type column. Where several lines relate to the same peptide, individual lines indicate different ionization states of the same peptide which may be used. Retention times are indicated in minutes normalized to retention times of a set of peptides as given in table 2.

| protein | seqID | seq | charge | ioncodes | ionintensities | retention time |
|---|---|---|---|---|---|---|
| STK19 | 166 | DAGSWWLAVPGAGR | 2 | y5_1, y7_1, y8_1, y9_1, y6_1 | 100, 71, 57, 52, 29 | 37.3 |
| STK19 | 167 | GLFEDALPPIVLR | 2 | y6_1, b12_2, y7_1, y8_1, y5_1 | 100, 6, 5, 2, 1 | 40.7 |
| TEC | 168 | DSSQPGLYTVSLYTK | 2 | y11_1, y8_1, y11_2, y5_1, y7_1 | 100, 27, 18, 15, 11 | 29.5 |
| TEC | 169 | NDDGVIPCQNK | 2 | y5_1, y6_1, y9_1, y4_1, y8_1 | 100, 24, 7, 6, 2 | 16.4 |
| TGFR2 | 170 | DYEPPFGSK | 2 | y6_1, y7_1, y5_1, y4_1, b3_1 | 100, 29, 15, 2, 1 | 21.5 |
| TGFR2 | 171 | LPYHDFILEDAASPK | 3 | b6_1, y7_1, b7_1, y8_1, y6_1 | 100, 96, 83, 76, 74 | 29.5 |
| TGFR2 | 172 | NDLTCCLCDFGLSLR | 2 | y6_1, y7_1, y8_1, y5_1, y9_1 | 100, 24, 22, 14, 10 | 38.7 |
| TGFR2 | 173 | SVNNDMIVTDNNGAVK | 2 | y8_1, b11_2, y7_1, b12_2, b5_1 | 100, 53, 50, 33, 30 | 14.7 |
| TGFR2 | 174 | YMAPEVLESR | 2 | y7_1, y8_1, y7_2, y4_1, y8_2 | 100, 25, 22, 13, 7 | 25.3 |
| TIF1A | 175 | LIFQNCAEFNEPDSEVANAGIK | 2 | y11_1, y6_1, y10_2, y7_1, y9_1 | 100, 45, 33, 22, 18 | 31.6 |
| TIF1A | 175 | LIFQNCAEFNEPDSEVANAGIK | 3 | y11_1, y6_1, b8_1, y11_2, b7_1 | 100, 42, 19, 17, 16 | 31.6 |
| TIF1A | 176 | LMQQQQEVAGLSK | 2 | y5_1, y4_1, y7_1, y11_1, | 100, 45, 36, 27 | 20.9 |
| TIF1A | 177 | SDAPDSTGDQPGLHQDNSSNGK | 2 | y6_1, y20_2, b6_1, y12_1, y17_2 | 100, 99, 98, 44, 38 | 10.6 |
| TIF1A | 177 | SDAPDSTGDQPGLHQDNSSNGK | 3 | y6_1, b6_1, y19_2, b7_1, y15_2 | 100, 91, 82, 70, 67 | 10.6 |
| TRI33 | 178 | LLQQQNDITGLSR | 2 | y5_1, y8_1, y4_1, y9_1, y6_1 | 100, 81, 57, 51, 42 | 24.8 |
| TRI33 | 179 | TEPADMNESCK | 2 | y9_2, y9_1, y7_1, y6_1, y8_1 | 100, 40, 17, 14, 4 | 12.8 |
| TRI33 | 179 | TEPADMNESCK | 3 | y4_1, y5_1, y3_1, y9_2, b5_1 | 100, 91, 81, 74, 55 | 12.8 |

TABLE 2

Retention times of table 1 are indicated in minutes normalized to retention times of the set of peptides as given in table 2, where corresponding retention times are given in minutes in a linear gradient of solvent as described above. By linear regression to these retention times values in table 1 can be transferred to any other linear chromatographic system.

| seqID | Sequence | retention time [min] |
|---|---|---|
| 180 | AAVYHHFISDGVR | 20.27 |
| 181 | HIQNIDIQHLAGK | 23.21 |
| 182 | GGQEHFAHLLILR | 28.4 |
| 183 | TEVSSNHVLIYLDK | 27.47 |

TABLE 2-continued

Retention times of table 1 are indicated in minutes normalized to retention times of the set of peptides as given in table 2, where corresponding retention times are given in minutes in a linear gradient of solvent as described above. By linear regression to these retention times values in table 1 can be transferred to any other linear chromatographic system.

| seqID | Sequence | retention time [min] |
|---|---|---|
| 184 | TEHPFTVEEFVLPK | 34.1 |
| 185 | NQGNTWLTAFVLK | 39.7 |
| 186 | LVAYYTLIGASGQR | 31.97 |
| 187 | TTNIQGINLLFSSR | 36.3 |

The invention claimed is:

1. A Method for the determination of an SRM assay for the detection and/or quantification of one or more peptides and/or proteins including the following steps:
   (1) preparation of a mixture of peptides in that a protein/peptide of interest, a group of proteins/peptides of interest, a subproteome or a whole proteome, is cleaved and/or digested, optionally followed by purification/separation/enrichment, to form said mixture of peptides, unique association at least one peptide of the protein of interest or a target protein of said group of proteins of interest or of said whole proteome from said mixture in a mass spectrometry experiment, wherein it is associated in terms of differential quantitative behaviour under different experimental conditions;
   (2) synthesis or generation of this at least one peptide essentially without subsequent purification;
   (3) analysis of this at least one unpurified peptide by selected reaction monitoring, or liquid-chromatography-coupled selected reaction monitoring;
   (4) development, validation and/or optimisation of the corresponding assay of the at least one peptide with determination of the SRM coordinates for a peptide/protein of interest and/or of a regulator of interest.

2. The method according to claim 1, wherein the different experimental conditions of step (1) are selected from the group of: different origin, derivation, disease, regulation of one single desired protein and/or group of proteins of interest or whole proteome.

3. The method according to claim 1, wherein the group of proteins of interest or peptides of interest comprises one or several specific classes or types of proteins or peptides which are selected or enriched by using purification or separation or enrichment steps.

4. The method according to claim 1, wherein the unpurified peptide is either synthesised in step (2), or generated by recombinant expression or derived by digesting recombinantly expressed proteins which contain the peptide or protein or group of proteins or proteome of interest, or by another chemical/biological/physical method.

5. The method according to claim 1, wherein in the unpurified peptide preparation made in step (2) and/or used in steps (3) and/or (4) the peptide of interest is present in less than 99% by weight.

6. The method according to claim 1, wherein in step (3) validation of the assay is achieved, either by analogy with the properties of the peptide standard or by acquiring fragmentation spectra or where fragmentation spectra are additionally acquired to select suitable peptide fragments.

7. The method according to claim 1, wherein in step (1) use is made of prior proteomics datasets, including previously acquired peptide fragmentation spectra, or of bioinformatic.

8. The method according to claim 1, wherein in step (4) at least one of the group of the following parameters of the SRM assay is determined: best responding peptides, preferred charge state and associated mass-to-charge ratio (m/z), corresponding elution times, best responding fragments and associated charge state and m/z value, fragment/transitions relative intensities, mass spectrometer or another parameter which increases the specificity, sensitivity, throughput of the assay(s).

9. The method according to claim 1, wherein after step (4) a heavy-labelled analogue of the selected peptide is synthesised to be used as an internal standard to achieve absolute quantification of a protein of interest.

10. The method according to claim 1, wherein for the absolute quantification of a protein of interest at step (2) or after step (4) the following steps are used:

(5) the peptide(s)/protein(s) of interest is synthesized without subsequent purification in a tagged-form, and the unpurified tagged-peptide is then subjected to enzymatic digestion under release of the tag in a stoichiometric amount to the peptide of interest;
(6) addition of a quantified heavy-labelled peptide analogue of the tag to the peptide sample in known amount and the tag and correspondingly the peptide of interest is quantified by mass spectrometry, wherein the heavy labelled analogue of the tag can be added prior or after digestion;
(7) addition of the accurately quantified, heavy-labelled peptide(s) to a protein sample and validation and/or optimisation of the SRM assay(s) for the corresponding proteins using the above steps (1)-(4) to achieve absolute quantification of the endogenous levels of the proteins.

11. The method according to claim 10, wherein as a tag in step (5) a short amino acid sequence or another quantifiable tag, is added to the sequence of each peptide of interest, separated by a site of specific enzymatic, chemical or physical cleavage.

12. The method according to claim 1, wherein a plurality of assays each for individual peptides of interest is determined according to steps (1)-(4), and/or where steps (3) and (4) are conducted either on each individual peptide preparation or on mixtures of them or on mixtures of the peptide(s) with any other sample.

13. Method of analysis of a protein sample of interest using at least one assay for peptides of interest as determined using a method according to claim 1, wherein SRM or time-constrained SRM are used and adapted elution times and possibly further parameters according to the assays are used to trigger acquisition of the set of selected SRM traces according to the assays.

14. The method according to claim 12, for the analysis and/or comparison of protein samples of wild-type or physiological or unregulated origin with protein samples of mutant, defective/pathological or regulated origin.

15. The method according to claim 13, wherein for absolute quantification of a protein of interest
(5) the peptide or protein (s) of interest is/are synthesized or generated essentially without subsequent purification in a tagged-form, and the unpurified tagged-peptide is then subjected to cleavage or enzymatic digestion under release of the tag in a stoichiometric amount to the peptide of interest;
(6) a quantified heavy-labelled peptide analogue of the tag is added to the peptide sample in known amount and the tag and correspondingly the peptide of interest is quantified, wherein a heavy labelled analogue of the tag can be added prior or after digestion; and
(7) the accurately quantified, heavy-labelled peptide(s) is added to the protein sample to achieve absolute quantification of the peptide (s) of interest and thus indirectly of the endogenous levels of the proteins of interest.

16. The method according to claim 1, wherein the different experimental conditions of step (1) are given by different origin and/or derivation and/or disease and/or regulation of one single desired protein and/or group of proteins of interest or whole proteome wherein the different regulation is that the single desired protein and/or group of proteins of interest or whole proteome is based on influenced, modified and/or diseased cells, tissues and/or body fluids of an organism, wherein the single desired protein and/or group of proteins of interest or whole proteome is based on a proteome derived from a genome in which a gene was knocked-out or mutated, or is based on a proteome in which a gene was knocked down or over expressed, or is based on a proteome in which the single desired protein or the group of proteins of interest were inhibited or activated by a biological, physical or chemical means, or is based on a proteome from diseased cells or tissues or body fluids in which any gene or protein affecting biological pathways was mutated or disregulated.

17. The method according to claim 1, wherein the different experimental conditions of step (1) are given by different origin and/or derivation and/or disease and/or regulation of one single desired protein and/or group of proteins of interest or whole proteome wherein the different regulation is that the single desired protein and/or group of proteins of interest or whole proteome is based on influenced, modified and/or diseased cells, tissues and/or body fluids of an organism, wherein the single desired protein and/or group of proteins of interest or whole proteome is based on a proteome derived from a genome in which a gene was knocked-out or mutated, or is based on a proteome in which a gene was knocked down or over expressed, or is based on a proteome in which the single desired protein or the group of proteins of interest were inhibited or activated by a biological, physical or chemical means, by means of inhibitors or activators or is based on a proteome from diseased cells or tissues or body fluids in which any gene or protein affecting biological pathways was mutated and/or disregulated.

18. A method according to claim 1, wherein the group of proteins of interest or peptides of interest comprises one or several specific classes or types of proteins or peptides which are selected or enriched by using purification or separation or enrichment steps, wherein such a separation or enrichment involves the separation of a specific type or proteins selected from the group of phosphoproteins, phosphopeptides, glycoproteins, glycopeptides, sulphorylated proteins, sulphorylated peptides.

19. A method according to claim 1, wherein the unpurified peptide is synthesised in step (2), on a micro-scale by using solid-phase synthesis essentially without subsequent purification.

20. A method according to claim 1, wherein in the unpurified peptide preparation made in step (2) and/or used in steps (3) and/or (4) the peptide of interest is present in less than 85%.

21. A method according to claim 1, wherein in the unpurified peptide preparation made in step (2) and/or used in steps (3) and/or (4) the peptide of interest is present in less than 90%, wherein in the preparation the peptide of interest is present in the range of 5-85%.

22. A method according to claim 1, wherein in step (3) validation of the assay is achieved, either by analogy with the properties of the peptide standard namely coelution on a chromatographic time scale, analogous fragmentation pattern, which is either synthetic or recombinantly expressed or by acquiring fragmentation spectra or where fragmentation spectra are additionally acquired to select suitable peptide fragments.

23. A method according to claim 1, wherein in step (1) use is made of prior proteomics datasets, including previously acquired peptide fragmentation spectra, or of bioinformatic prediction by screening proteomics data repositories, literature or of computational prediction of the MS detectability, using algorithms or where peptides are selected based on the knowledge about the cleavage specificity of the enzymatic, chemical or physical agent used to cleave the proteins into peptides.

24. A method according to claim 1, wherein in step (4) at least one of the group of the following parameters of the SRM assay is determined: best responding peptides, preferred charge state and associated mass-to-charge ratio (m/z), corresponding elution times, best responding fragments and associated charge state and m/z value, fragment/transitions relative intensities, mass spectrometer parameters such as optimal collision energies and/or collision gas pressure and/or declustering potentials or another parameter which increases the specificity, sensitivity, throughput of the assay(s).

25. A method according to claim 1, wherein for the absolute quantification of a protein of interest at step (2) or after step (4) the following steps are used:
   (5) the peptide(s)/protein(s) of interest is synthesized without subsequent purification in a tagged-form with a heavy labeled amino acid at the C-terminus, and the unpurified tagged-peptide is then subjected to enzymatic digestion under release of the tag in a stoichiometric amount to the peptide of interest;
   (6) addition of a quantified heavy-labelled peptide analogue of the tag to the peptide sample in known amount and the tag and correspondingly the peptide of interest is quantified by mass spectrometry, wherein the heavy labelled analogue of the tag can be added prior or after digestion; and use of the released peptide to optimize/validate the SRM assay;
   (7) addition of the accurately quantified, heavy-labelled peptide(s) to a protein sample and validation and/or optimisation of the SRM assay(s) for the corresponding proteins using the above steps (1)-(4) to achieve absolute quantification of the endogenous levels of the proteins.

26. A method according to claim 10, wherein as a tag in step (5) a short amino acid sequence or another quantifiable tag as a fluorophor, is added to the sequence of each peptide of interest, separated by a site of specific enzymatic, chemical or physical cleavage such as tryptic cleavage or another cleavable group including acid-labile or photo-cleavable linkers.

27. Method of analysis of a protein sample of interest using a multitude of assays for peptides of interest as determined using a method according to claim 1, wherein SRM or time-constrained SRM are used and adapted elution times and possibly further parameters according to the assays are used to trigger acquisition of the set of selected SRM traces according to the assays.

28. Method according to claim 12, for the analysis and/or comparison of protein samples of wild-type or physiological or unregulated origin with protein samples of mutant, defective/pathological or regulated origin, wherein regulation is induced by a pharmaceutically, chemically or biologically active substance.

29. Method according to claim 13, wherein for absolute quantification of a protein of interest (5) the peptide/protein (s) of interest is/are synthesized/generated essentially without subsequent purification in a tagged-form with a heavy labelled amino acid at the C-terminus, and the unpurified tagged-peptide is then subjected to cleavage/enzymatic digestion under release of the tag in a stoichiometric amount to the peptide of interest;
   (6) a quantified heavy-labelled peptide analogue of the tag is added to the peptide sample in known amount and the tag and correspondingly the peptide of interest is quantified, by mass spectrometry, wherein the heavy labelled analogue of the tag can be added prior or after digestion; and
   (7) the accurately quantified, heavy-labelled peptide(s) is added to the protein sample to achieve absolute quantification of the peptide (s) of interest and thus indirectly of the endogenous levels of the proteins of interest.

* * * * *

SEQUENCE LISTING

<160> NUMBER OF SEQ ID NOS: 189

<210> SEQ ID NO 1
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 1

Ala Ser Asp Phe Gly Val Asn Ile Thr Glu Asp Val Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic oligopeptide

<400> SEQUENCE: 2

Thr Ala Gly Lys
1

<210> SEQ ID NO 3
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 3

Thr Ala Gly Lys Ala Ser Asp Phe Gly Val Asn Ile Thr Glu Asp Val
1               5                   10                  15

Lys

<210> SEQ ID NO 4
<211> LENGTH: 11
<212> TYPE: PRT
<213> ORGANISM: Homo Sapiens

<400> SEQUENCE: 4

Asn Cys Leu Val Gly Glu Asn His Val Val Lys
1               5                   10

```
<210> SEQ ID NO 5
<211> LENGTH: 15
<212> TYPE: PRT
<213> ORGANISM: Homo Sapiens

<400> SEQUENCE: 5

Trp Thr Ala Pro Glu Ser Leu Ala Tyr Asn Thr Phe Ser Ile Lys
1               5                   10                  15

<210> SEQ ID NO 6
<211> LENGTH: 19
<212> TYPE: PRT
<213> ORGANISM: Homo Sapiens

<400> SEQUENCE: 6

Cys Gly Ser Pro Ser Asp Ser Ser Thr Thr Glu Glu Met Glu Val Ala
1               5                   10                  15

Val Ser Lys

<210> SEQ ID NO 7
<211> LENGTH: 9
<212> TYPE: PRT
<213> ORGANISM: Homo Sapiens

<400> SEQUENCE: 7

Leu Gly Gly Gly Pro Ser Asp Ala Lys
1               5

<210> SEQ ID NO 8
<211> LENGTH: 9
<212> TYPE: PRT
<213> ORGANISM: Homo Sapiens

<400> SEQUENCE: 8

Ser Asp Gly Ser Phe Ile Gly Tyr Lys
1               5

<210> SEQ ID NO 9
<211> LENGTH: 12
<212> TYPE: PRT
<213> ORGANISM: Homo Sapiens

<400> SEQUENCE: 9

Tyr Asp Ser Leu Gly Leu Leu Glu Leu Asp Gln Arg
1               5                   10

<210> SEQ ID NO 10
<211> LENGTH: 16
<212> TYPE: PRT
<213> ORGANISM: Homo Sapiens

<400> SEQUENCE: 10

Asp Leu Glu Gln Asp Glu Ala Phe Ile Pro Val Gly Glu Ser Leu Lys
1               5                   10                  15

<210> SEQ ID NO 11
<211> LENGTH: 14
<212> TYPE: PRT
<213> ORGANISM: Homo Sapiens

<400> SEQUENCE: 11

Asn Gly Ser Cys Cys Ile Ala Asp Leu Gly Leu Ala Val Lys
1               5                   10
```

```
<210> SEQ ID NO 12
<211> LENGTH: 17
<212> TYPE: PRT
<213> ORGANISM: Homo Sapiens

<400> SEQUENCE: 12

Ser Glu Asn Gly Val Thr Leu Ala Pro Glu Asp Thr Leu Pro Phe Leu
1               5                   10                  15
Lys

<210> SEQ ID NO 13
<211> LENGTH: 9
<212> TYPE: PRT
<213> ORGANISM: Homo Sapiens

<400> SEQUENCE: 13

Tyr Glu Gly Ser Asp Phe Gln Cys Lys
1               5

<210> SEQ ID NO 14
<211> LENGTH: 13
<212> TYPE: PRT
<213> ORGANISM: Homo Sapiens

<400> SEQUENCE: 14

Leu Met Thr Glu Cys Trp Ala His Asn Pro Ala Ser Arg
1               5                   10

<210> SEQ ID NO 15
<211> LENGTH: 14
<212> TYPE: PRT
<213> ORGANISM: Homo Sapiens

<400> SEQUENCE: 15

Asn Gly Thr Cys Cys Ile Ala Asp Leu Gly Leu Ala Val Lys
1               5                   10

<210> SEQ ID NO 16
<211> LENGTH: 10
<212> TYPE: PRT
<213> ORGANISM: Homo Sapiens

<400> SEQUENCE: 16

Asp Ala Gln Glu Phe Gly Ala Asp Val Arg
1               5                   10

<210> SEQ ID NO 17
<211> LENGTH: 13
<212> TYPE: PRT
<213> ORGANISM: Homo Sapiens

<400> SEQUENCE: 17

Asp Val Pro Asp Ser Gln Gln His Pro Ala Pro Glu Lys
1               5                   10

<210> SEQ ID NO 18
<211> LENGTH: 14
<212> TYPE: PRT
<213> ORGANISM: Homo Sapiens

<400> SEQUENCE: 18

Gly Gly Gly Ala Gly Glu Gln Pro Pro Pro Ser Ala Arg
1               5                   10
```

```
<210> SEQ ID NO 19
<211> LENGTH: 17
<212> TYPE: PRT
<213> ORGANISM: Homo Sapiens

<400> SEQUENCE: 19

Ser Pro Val Phe Ser Phe Ser Pro Glu Pro Gly Ala Gly Asp Glu Ala
1               5                   10                  15

Arg

<210> SEQ ID NO 20
<211> LENGTH: 18
<212> TYPE: PRT
<213> ORGANISM: Homo Sapiens

<400> SEQUENCE: 20

Ser Val Ser Gly Ala Ser Thr Gly Leu Ser Ser Ser Pro Leu Ser Ser
1               5                   10                  15

Pro Arg

<210> SEQ ID NO 21
<211> LENGTH: 12
<212> TYPE: PRT
<213> ORGANISM: Homo Sapiens

<400> SEQUENCE: 21

Tyr Pro Ser Cys Glu Asp Gln Asp Leu Pro Pro Arg
1               5                   10

<210> SEQ ID NO 22
<211> LENGTH: 13
<212> TYPE: PRT
<213> ORGANISM: Homo Sapiens

<400> SEQUENCE: 22

Phe Tyr Thr Gly Asn Asp Pro Leu Asp Val Trp Asp Arg
1               5                   10

<210> SEQ ID NO 23
<211> LENGTH: 14
<212> TYPE: PRT
<213> ORGANISM: Homo Sapiens

<400> SEQUENCE: 23

Tyr Ile Ser Trp Thr Glu Gln Asn Tyr Pro Gln Gly Gly Lys
1               5                   10

<210> SEQ ID NO 24
<211> LENGTH: 13
<212> TYPE: PRT
<213> ORGANISM: Homo Sapiens

<400> SEQUENCE: 24

Gly Glu Glu Ala Ala Gly Tyr Ala Gln Glu Ser Gln Arg
1               5                   10

<210> SEQ ID NO 25
<211> LENGTH: 20
<212> TYPE: PRT
<213> ORGANISM: Homo Sapiens

<400> SEQUENCE: 25

Ile Thr Ala Glu Glu Ala Ile Ser His Glu Trp Ile Ser Gly Asn Ala
1               5                   10                  15
```

Ala Ser Asp Lys
            20

<210> SEQ ID NO 26
<211> LENGTH: 13
<212> TYPE: PRT
<213> ORGANISM: Homo Sapiens

<400> SEQUENCE: 26

Gln Val Leu Glu Ala Val Ala Tyr Leu His Ser Leu Lys
1               5                   10

<210> SEQ ID NO 27
<211> LENGTH: 9
<212> TYPE: PRT
<213> ORGANISM: Homo Sapiens

<400> SEQUENCE: 27

Thr Glu Glu Phe Cys Glu Ile Phe Arg
1               5

<210> SEQ ID NO 28
<211> LENGTH: 12
<212> TYPE: PRT
<213> ORGANISM: Homo Sapiens

<400> SEQUENCE: 28

Ala Pro Pro Pro Gly Leu Pro Ala Glu Thr Ile Lys
1               5                   10

<210> SEQ ID NO 29
<211> LENGTH: 16
<212> TYPE: PRT
<213> ORGANISM: Homo Sapiens

<400> SEQUENCE: 29

Asp Leu Lys Pro Glu Asn Ile Leu Val Thr Ser Gly Gly Thr Val Lys
1               5                   10                  15

<210> SEQ ID NO 30
<211> LENGTH: 17
<212> TYPE: PRT
<213> ORGANISM: Homo Sapiens

<400> SEQUENCE: 30

Tyr Glu Pro Val Ala Glu Ile Gly Val Gly Ala Tyr Gly Thr Val Tyr
1               5                   10                  15

Lys

<210> SEQ ID NO 31
<211> LENGTH: 18
<212> TYPE: PRT
<213> ORGANISM: Homo Sapiens

<400> SEQUENCE: 31

Ala Asp Gln Gln Tyr Glu Cys Val Ala Glu Ile Gly Glu Gly Ala Tyr
1               5                   10                  15

Gly Lys

<210> SEQ ID NO 32
<211> LENGTH: 10
<212> TYPE: PRT
<213> ORGANISM: Homo Sapiens

<400> SEQUENCE: 32

Gly Ser Ser Asp Val Asp Gln Leu Gly Lys
1               5                   10

<210> SEQ ID NO 33
<211> LENGTH: 12
<212> TYPE: PRT
<213> ORGANISM: Homo Sapiens

<400> SEQUENCE: 33

His Leu Glu Thr Phe Glu His Pro Asn Val Val Arg
1               5                   10

<210> SEQ ID NO 34
<211> LENGTH: 17
<212> TYPE: PRT
<213> ORGANISM: Homo Sapiens

<400> SEQUENCE: 34

Ile Ser Ala Tyr Ser Ala Leu Ser His Pro Tyr Phe Gln Asp Leu Glu
1               5                   10                  15

Arg

<210> SEQ ID NO 35
<211> LENGTH: 11
<212> TYPE: PRT
<213> ORGANISM: Homo Sapiens

<400> SEQUENCE: 35

Glu Phe Leu Thr Glu Glu Glu Pro Asp Asp Lys
1               5                   10

<210> SEQ ID NO 36
<211> LENGTH: 9
<212> TYPE: PRT
<213> ORGANISM: Homo Sapiens

<400> SEQUENCE: 36

Met Pro Glu His Ser Thr Leu Met Lys
1               5

<210> SEQ ID NO 37
<211> LENGTH: 12
<212> TYPE: PRT
<213> ORGANISM: Homo Sapiens

<400> SEQUENCE: 37

Thr Ser Asn Pro Tyr His His Asp Gln Leu Asp Arg
1               5                   10

<210> SEQ ID NO 38
<211> LENGTH: 12
<212> TYPE: PRT
<213> ORGANISM: Homo Sapiens

<400> SEQUENCE: 38

His Glu Asn Leu Val Asn Leu Leu Glu Val Cys Lys
1               5                   10

<210> SEQ ID NO 39
<211> LENGTH: 16
<212> TYPE: PRT
<213> ORGANISM: Homo Sapiens

<400> SEQUENCE: 39

Thr Leu Ala Ala Pro Gly Glu Val Tyr Thr Asp Tyr Val Ala Thr Arg
1               5                   10                  15

<210> SEQ ID NO 40
<211> LENGTH: 17
<212> TYPE: PRT
<213> ORGANISM: Homo Sapiens

<400> SEQUENCE: 40

Tyr Glu Asn Leu Gly Leu Val Gly Glu Gly Ser Tyr Gly Met Val Met
1               5                   10                  15

Lys

<210> SEQ ID NO 41
<211> LENGTH: 15
<212> TYPE: PRT
<213> ORGANISM: Homo Sapiens

<400> SEQUENCE: 41

Arg Pro Leu Asn Asn Asn Ser Glu Ile Ala Leu Ser Leu Ser Arg
1               5                   10                  15

<210> SEQ ID NO 42
<211> LENGTH: 11
<212> TYPE: PRT
<213> ORGANISM: Homo Sapiens

<400> SEQUENCE: 42

Thr Leu Gly Ser Gly Ala Cys Gly Glu Val Lys
1               5                   10

<210> SEQ ID NO 43
<211> LENGTH: 14
<212> TYPE: PRT
<213> ORGANISM: Homo Sapiens

<400> SEQUENCE: 43

Tyr Asn Phe Ile Pro Glu Val Trp Ala Glu Val Ser Glu Lys
1               5                   10

<210> SEQ ID NO 44
<211> LENGTH: 13
<212> TYPE: PRT
<213> ORGANISM: Homo Sapiens

<400> SEQUENCE: 44

Glu Ser Leu Thr Glu Asp Glu Ala Thr Gln Phe Leu Lys
1               5                   10

<210> SEQ ID NO 45
<211> LENGTH: 16
<212> TYPE: PRT
<213> ORGANISM: Homo Sapiens

<400> SEQUENCE: 45

Leu Cys His Glu Asp Val Glu Ala Leu Ala Ala Ile Tyr Glu Glu Lys
1               5                   10                  15

<210> SEQ ID NO 46
<211> LENGTH: 13
<212> TYPE: PRT
<213> ORGANISM: Homo Sapiens

<400> SEQUENCE: 46

Val Leu Glu Glu Ala Ala Ala Ala Glu Glu Gly Leu Arg

```
<210> SEQ ID NO 47
<211> LENGTH: 13
<212> TYPE: PRT
<213> ORGANISM: Homo Sapiens

<400> SEQUENCE: 47

Gly Gly Asp Leu Phe Asp Ala Ile Thr Ser Thr Asn Lys
1               5                   10

<210> SEQ ID NO 48
<211> LENGTH: 22
<212> TYPE: PRT
<213> ORGANISM: Homo Sapiens

<400> SEQUENCE: 48

Ile Ser Ser Leu Asp Gln Leu Val Glu Gly Glu Ser Tyr Val Cys Gly
1               5                   10                  15

Ser Ile Glu Pro Phe Lys
            20

<210> SEQ ID NO 49
<211> LENGTH: 11
<212> TYPE: PRT
<213> ORGANISM: Homo Sapiens

<400> SEQUENCE: 49

Ser Phe Glu Ala Leu Leu Ala Asp Leu Thr Arg
1               5                   10

<210> SEQ ID NO 50
<211> LENGTH: 13
<212> TYPE: PRT
<213> ORGANISM: Homo Sapiens

<400> SEQUENCE: 50

Tyr Gln Asp Asp Phe Leu Leu Asp Glu Ser Glu Cys Arg
1               5                   10

<210> SEQ ID NO 51
<211> LENGTH: 13
<212> TYPE: PRT
<213> ORGANISM: Homo Sapiens

<400> SEQUENCE: 51

Glu Ile Ser Asp Gly Asp Val Ile Ile Ser Gly Asn Lys
1               5                   10

<210> SEQ ID NO 52
<211> LENGTH: 11
<212> TYPE: PRT
<213> ORGANISM: Homo Sapiens

<400> SEQUENCE: 52

Val Cys Asn Gly Ile Gly Ile Gly Glu Phe Lys
1               5                   10

<210> SEQ ID NO 53
<211> LENGTH: 13
<212> TYPE: PRT
<213> ORGANISM: Homo Sapiens

<400> SEQUENCE: 53

Asp Cys Asn Ser Ile Pro Leu Val Leu Gly Thr Cys Lys
```

```
                1               5                   10
```

<210> SEQ ID NO 54
<211> LENGTH: 10
<212> TYPE: PRT
<213> ORGANISM: Homo Sapiens

<400> SEQUENCE: 54

```
Phe Glu Gln Ile Val Ser Ile Leu Asp Lys
1               5                   10
```

<210> SEQ ID NO 55
<211> LENGTH: 14
<212> TYPE: PRT
<213> ORGANISM: Homo Sapiens

<400> SEQUENCE: 55

```
Val Val Gly Ala Gly Glu Phe Gly Glu Val Cys Ser Gly Arg
1               5                   10
```

<210> SEQ ID NO 56
<211> LENGTH: 10
<212> TYPE: PRT
<213> ORGANISM: Homo Sapiens

<400> SEQUENCE: 56

```
Phe Glu Gln Ile Val Gly Ile Leu Asp Lys
1               5                   10
```

<210> SEQ ID NO 57
<211> LENGTH: 16
<212> TYPE: PRT
<213> ORGANISM: Homo Sapiens

<400> SEQUENCE: 57

```
Gly Thr Cys Val Ser Ser Ala Glu Glu Glu Ala Glu Asn Ala Pro Arg
1               5                   10                  15
```

<210> SEQ ID NO 58
<211> LENGTH: 12
<212> TYPE: PRT
<213> ORGANISM: Homo Sapiens

<400> SEQUENCE: 58

```
Leu Asp Val Ala Thr Leu Glu Glu Ala Thr Gly Lys
1               5                   10
```

<210> SEQ ID NO 59
<211> LENGTH: 13
<212> TYPE: PRT
<213> ORGANISM: Homo Sapiens

<400> SEQUENCE: 59

```
Asp Cys Asn Ser Met Pro Gly Val Leu Gly Thr Cys Lys
1               5                   10
```

<210> SEQ ID NO 60
<211> LENGTH: 15
<212> TYPE: PRT
<213> ORGANISM: Homo Sapiens

<400> SEQUENCE: 60

```
Met Tyr Cys Ser Ala Glu Gly Glu Trp Leu Val Pro Ile Gly Lys
1               5                   10                  15
```

```
<210> SEQ ID NO 61
<211> LENGTH: 13
<212> TYPE: PRT
<213> ORGANISM: Homo Sapiens

<400> SEQUENCE: 61

Glu Ala Leu Leu Ser Gly Ile Ser Ala Leu Gln Ala Arg
1               5                   10

<210> SEQ ID NO 62
<211> LENGTH: 12
<212> TYPE: PRT
<213> ORGANISM: Homo Sapiens

<400> SEQUENCE: 62

Cys Pro Ser Ser Gly Thr Pro Asn Pro Thr Leu Arg
1               5                   10

<210> SEQ ID NO 63
<211> LENGTH: 13
<212> TYPE: PRT
<213> ORGANISM: Homo Sapiens

<400> SEQUENCE: 63

Ile Gly Pro Asp Asn Leu Pro Tyr Val Gln Ile Leu Lys
1               5                   10

<210> SEQ ID NO 64
<211> LENGTH: 13
<212> TYPE: PRT
<213> ORGANISM: Homo Sapiens

<400> SEQUENCE: 64

Thr Val Ala Leu Gly Ser Asn Val Glu Phe Met Cys Lys
1               5                   10

<210> SEQ ID NO 65
<211> LENGTH: 11
<212> TYPE: PRT
<213> ORGANISM: Homo Sapiens

<400> SEQUENCE: 65

Asp Leu Val Ser Cys Thr Tyr Gln Leu Ala Arg
1               5                   10

<210> SEQ ID NO 66
<211> LENGTH: 25
<212> TYPE: PRT
<213> ORGANISM: Homo Sapiens

<400> SEQUENCE: 66

Leu Thr Leu Gly Lys Pro Leu Glu Gly Cys Phe Gly Gln Val Val
1               5                   10                  15

Met Ala Glu Ala Val Gly Ile Asp Lys
                20                  25

<210> SEQ ID NO 67
<211> LENGTH: 13
<212> TYPE: PRT
<213> ORGANISM: Homo Sapiens

<400> SEQUENCE: 67

Asp Leu Ala Asp Leu Val Ser Glu Met Glu Val Met Lys
1               5                   10
```

```
<210> SEQ ID NO 68
<211> LENGTH: 13
<212> TYPE: PRT
<213> ORGANISM: Homo Sapiens

<400> SEQUENCE: 68

Arg Pro Pro Gly Pro Asp Leu Ser Pro Asp Gly Pro Arg
1               5                   10

<210> SEQ ID NO 69
<211> LENGTH: 13
<212> TYPE: PRT
<213> ORGANISM: Homo Sapiens

<400> SEQUENCE: 69

Val Leu Leu Ala Val Ser Glu Glu Tyr Leu Asp Leu Arg
1               5                   10

<210> SEQ ID NO 70
<211> LENGTH: 15
<212> TYPE: PRT
<213> ORGANISM: Homo Sapiens

<400> SEQUENCE: 70

His Ser Ser Leu Asn Cys Gln Pro His Phe Asp Leu Gln Asn Arg
1               5                   10                  15

<210> SEQ ID NO 71
<211> LENGTH: 19
<212> TYPE: PRT
<213> ORGANISM: Homo Sapiens

<400> SEQUENCE: 71

Gly Gly Ile Leu Ala Ile Ala Ser Leu Ile Gly Val Glu Gly Gly Asn
1               5                   10                  15

Ala Thr Arg

<210> SEQ ID NO 72
<211> LENGTH: 11
<212> TYPE: PRT
<213> ORGANISM: Homo Sapiens

<400> SEQUENCE: 72

Asp Gly Ser Leu Asn Gln Ser Ser Gly Tyr Arg
1               5                   10

<210> SEQ ID NO 73
<211> LENGTH: 9
<212> TYPE: PRT
<213> ORGANISM: Homo Sapiens

<400> SEQUENCE: 73

Gln Leu Leu Ser Phe Gly Asn Pro Arg
1               5

<210> SEQ ID NO 74
<211> LENGTH: 20
<212> TYPE: PRT
<213> ORGANISM: Homo Sapiens

<400> SEQUENCE: 74

Thr Leu Lys Pro Gly Thr Met Ser Pro Glu Ser Phe Leu Glu Glu Ala
1               5                   10                  15

Gln Ile Met Lys
            20
```

<210> SEQ ID NO 75
<211> LENGTH: 13
<212> TYPE: PRT
<213> ORGANISM: Homo Sapiens

<400> SEQUENCE: 75

Cys Ile Phe Ala Cys Glu Glu Met Ser Gly Glu Val Arg
1               5                   10

<210> SEQ ID NO 76
<211> LENGTH: 15
<212> TYPE: PRT
<213> ORGANISM: Homo Sapiens

<400> SEQUENCE: 76

Asp Leu Lys Pro Glu Asn Ile Val Leu Gln Asp Val Gly Gly Lys
1               5                   10                  15

<210> SEQ ID NO 77
<211> LENGTH: 14
<212> TYPE: PRT
<213> ORGANISM: Homo Sapiens

<400> SEQUENCE: 77

Ser Leu Ser Asp Cys Val Asn Tyr Ile Val Gln Asp Ser Lys
1               5                   10

<210> SEQ ID NO 78
<211> LENGTH: 10
<212> TYPE: PRT
<213> ORGANISM: Homo Sapiens

<400> SEQUENCE: 78

Thr Val Tyr Glu Gly Pro Phe Ala Ser Arg
1               5                   10

<210> SEQ ID NO 79
<211> LENGTH: 15
<212> TYPE: PRT
<213> ORGANISM: Homo Sapiens

<400> SEQUENCE: 79

Asp Leu Val Glu Glu Glu Ala Glu Val Ala Gly Val Ala Leu Arg
1               5                   10                  15

<210> SEQ ID NO 80
<211> LENGTH: 12
<212> TYPE: PRT
<213> ORGANISM: Homo Sapiens

<400> SEQUENCE: 80

Gly Thr Leu Ala Tyr Leu Pro Glu Glu Tyr Ile Lys
1               5                   10

<210> SEQ ID NO 81
<211> LENGTH: 11
<212> TYPE: PRT
<213> ORGANISM: Homo Sapiens

<400> SEQUENCE: 81

Ala Val Val Ser Glu Asn Asn Pro Cys Ile Lys
1               5                   10

<210> SEQ ID NO 82

```
<211> LENGTH: 18
<212> TYPE: PRT
<213> ORGANISM: Homo Sapiens

<400> SEQUENCE: 82

Glu Gly Ala Met Ser Glu Glu Asp Phe Ile Glu Glu Ala Glu Val Met
1               5                   10                  15

Met Lys

<210> SEQ ID NO 83
<211> LENGTH: 11
<212> TYPE: PRT
<213> ORGANISM: Homo Sapiens

<400> SEQUENCE: 83

Asn Cys Leu Val Gly Glu Asn Gln Val Ile Lys
1               5                   10

<210> SEQ ID NO 84
<211> LENGTH: 13
<212> TYPE: PRT
<213> ORGANISM: Homo Sapiens

<400> SEQUENCE: 84

Ser Pro Asn Asn Leu Glu Thr Tyr Glu Trp Tyr Asn Lys
1               5                   10

<210> SEQ ID NO 85
<211> LENGTH: 16
<212> TYPE: PRT
<213> ORGANISM: Homo Sapiens

<400> SEQUENCE: 85

Thr Leu Cys Gly Thr Pro Glu Tyr Ile Ala Pro Glu Val Leu Leu Arg
1               5                   10                  15

<210> SEQ ID NO 86
<211> LENGTH: 10
<212> TYPE: PRT
<213> ORGANISM: Homo Sapiens

<400> SEQUENCE: 86

Asp Glu Ser Gly Ser Pro Glu Ser Ile Arg
1               5                   10

<210> SEQ ID NO 87
<211> LENGTH: 11
<212> TYPE: PRT
<213> ORGANISM: Homo Sapiens

<400> SEQUENCE: 87

Glu Ala Ser Asp Val Leu Cys Thr Ile Thr Lys
1               5                   10

<210> SEQ ID NO 88
<211> LENGTH: 16
<212> TYPE: PRT
<213> ORGANISM: Homo Sapiens

<400> SEQUENCE: 88

Leu Gly Met Pro Gln Phe Leu Ser Gly Glu Ala Gln Ser Leu Leu Arg
1               5                   10                  15

<210> SEQ ID NO 89
<211> LENGTH: 12
```

```
<212> TYPE: PRT
<213> ORGANISM: Homo Sapiens

<400> SEQUENCE: 89

Glu Ala Pro Pro Cys His Leu Leu Ile Ile His Arg
1               5                   10

<210> SEQ ID NO 90
<211> LENGTH: 20
<212> TYPE: PRT
<213> ORGANISM: Homo Sapiens

<400> SEQUENCE: 90

Glu Glu Ala Glu Asp Tyr Leu Val Gln Gly Gly Met Ser Asp Gly Leu
1               5                   10                  15

Tyr Leu Leu Arg
            20

<210> SEQ ID NO 91
<211> LENGTH: 14
<212> TYPE: PRT
<213> ORGANISM: Homo Sapiens

<400> SEQUENCE: 91

Asn Tyr Leu Gly Gly Phe Ala Leu Ser Val Ala His Gly Arg
1               5                   10

<210> SEQ ID NO 92
<211> LENGTH: 23
<212> TYPE: PRT
<213> ORGANISM: Homo Sapiens

<400> SEQUENCE: 92

Gln Thr Trp Asn Leu Gln Gly Gln Ala Leu Glu Gln Ala Ile Ile Ser
1               5                   10                  15

Gln Lys Pro Gln Leu Glu Lys
            20

<210> SEQ ID NO 93
<211> LENGTH: 10
<212> TYPE: PRT
<213> ORGANISM: Homo Sapiens

<400> SEQUENCE: 93

Tyr Leu Glu Glu Ser Asn Phe Val His Arg
1               5                   10

<210> SEQ ID NO 94
<211> LENGTH: 13
<212> TYPE: PRT
<213> ORGANISM: Homo Sapiens

<400> SEQUENCE: 94

Ala Ala Asn Ile Leu Val Ser Asp Thr Leu Ser Cys Lys
1               5                   10

<210> SEQ ID NO 95
<211> LENGTH: 14
<212> TYPE: PRT
<213> ORGANISM: Homo Sapiens

<400> SEQUENCE: 95

Glu Ser Glu Ser Thr Ala Gly Ser Phe Ser Leu Ser Val Arg
1               5                   10
```

```
<210> SEQ ID NO 96
<211> LENGTH: 12
<212> TYPE: PRT
<213> ORGANISM: Homo Sapiens

<400> SEQUENCE: 96

His Tyr Thr Asn Ala Ser Asp Gly Leu Cys Thr Arg
1               5                   10

<210> SEQ ID NO 97
<211> LENGTH: 7
<212> TYPE: PRT
<213> ORGANISM: Homo Sapiens

<400> SEQUENCE: 97

Glu Ala Ala Glu Ile Met Arg
1               5

<210> SEQ ID NO 98
<211> LENGTH: 19
<212> TYPE: PRT
<213> ORGANISM: Homo Sapiens

<400> SEQUENCE: 98

Leu Gly Gln Tyr Gly Phe Pro Asn Pro Glu Trp Ser Glu Val Ser Glu
1               5                   10                  15

Asp Ala Lys

<210> SEQ ID NO 99
<211> LENGTH: 10
<212> TYPE: PRT
<213> ORGANISM: Homo Sapiens

<400> SEQUENCE: 99

Gln Val Leu Gly Leu Gly Val Asn Gly Lys
1               5                   10

<210> SEQ ID NO 100
<211> LENGTH: 14
<212> TYPE: PRT
<213> ORGANISM: Homo Sapiens

<400> SEQUENCE: 100

Gly Asp Leu Thr Ile Ala Asn Leu Gly Thr Ser Glu Gly Arg
1               5                   10

<210> SEQ ID NO 101
<211> LENGTH: 18
<212> TYPE: PRT
<213> ORGANISM: Homo Sapiens

<400> SEQUENCE: 101

Ile Thr Asp Ile Gly Glu Val Ser Gln Phe Leu Thr Glu Gly Ile Ile
1               5                   10                  15

Met Lys

<210> SEQ ID NO 102
<211> LENGTH: 13
<212> TYPE: PRT
<213> ORGANISM: Homo Sapiens

<400> SEQUENCE: 102

Val Phe Pro Asn Ser Ala Pro Leu Glu Gly Gly Thr Arg
1               5                   10
```

<210> SEQ ID NO 103
<211> LENGTH: 15
<212> TYPE: PRT
<213> ORGANISM: Homo Sapiens

<400> SEQUENCE: 103

Leu Phe Pro Asp Val Leu Phe Pro Ala Asp Ser Glu His Asn Lys
1               5                   10                  15

<210> SEQ ID NO 104
<211> LENGTH: 13
<212> TYPE: PRT
<213> ORGANISM: Homo Sapiens

<400> SEQUENCE: 104

Asn Ile Ile Gly Leu Leu Asn Val Phe Thr Pro Gln Lys
1               5                   10

<210> SEQ ID NO 105
<211> LENGTH: 8
<212> TYPE: PRT
<213> ORGANISM: Homo Sapiens

<400> SEQUENCE: 105

Tyr Ala Gly Tyr Ser Phe Glu Lys
1               5

<210> SEQ ID NO 106
<211> LENGTH: 16
<212> TYPE: PRT
<213> ORGANISM: Homo Sapiens

<400> SEQUENCE: 106

Gly Cys Val Ile Phe Gln Gly Thr Asp His Ile Asp Gln Trp Asn Lys
1               5                   10                  15

<210> SEQ ID NO 107
<211> LENGTH: 8
<212> TYPE: PRT
<213> ORGANISM: Homo Sapiens

<400> SEQUENCE: 107

Ile Ser Val Asp Glu Ala Leu Arg
1               5

<210> SEQ ID NO 108
<211> LENGTH: 14
<212> TYPE: PRT
<213> ORGANISM: Homo Sapiens

<400> SEQUENCE: 108

Val Ile Glu Gln Leu Gly Thr Pro Ser Ala Glu Phe Met Lys
1               5                   10

<210> SEQ ID NO 109
<211> LENGTH: 16
<212> TYPE: PRT
<213> ORGANISM: Homo Sapiens

<400> SEQUENCE: 109

Asp Leu Lys Pro Ser Asn Leu Ala Val Asn Glu Asp Cys Glu Leu Lys
1               5                   10                  15

<210> SEQ ID NO 110

```
<211> LENGTH: 15
<212> TYPE: PRT
<213> ORGANISM: Homo Sapiens

<400> SEQUENCE: 110

His Glu Asn Val Ile Gly Leu Leu Asp Val Phe Thr Pro Ala Arg
1               5                   10                  15

<210> SEQ ID NO 111
<211> LENGTH: 10
<212> TYPE: PRT
<213> ORGANISM: Homo Sapiens

<400> SEQUENCE: 111

Tyr Ile His Ser Ala Asp Ile Ile His Arg
1               5                   10

<210> SEQ ID NO 112
<211> LENGTH: 22
<212> TYPE: PRT
<213> ORGANISM: Homo Sapiens

<400> SEQUENCE: 112

Tyr Gln Asn Leu Ser Pro Val Gly Ser Gly Ala Tyr Gly Ser Val Cys
1               5                   10                  15

Ala Ala Phe Asp Thr Lys
            20

<210> SEQ ID NO 113
<211> LENGTH: 12
<212> TYPE: PRT
<213> ORGANISM: Homo Sapiens

<400> SEQUENCE: 113

Ser Ala Gly Cys Ala Ala Tyr Met Ala Pro Glu Arg
1               5                   10

<210> SEQ ID NO 114
<211> LENGTH: 13
<212> TYPE: PRT
<213> ORGANISM: Homo Sapiens

<400> SEQUENCE: 114

Tyr Glu Thr Leu Glu Val Asp Val Ala Ser Trp Phe Lys
1               5                   10

<210> SEQ ID NO 115
<211> LENGTH: 13
<212> TYPE: PRT
<213> ORGANISM: Homo Sapiens

<400> SEQUENCE: 115

Ala Ala Cys Leu Leu Asp Gly Val Pro Val Ala Leu Lys
1               5                   10

<210> SEQ ID NO 116
<211> LENGTH: 19
<212> TYPE: PRT
<213> ORGANISM: Homo Sapiens

<400> SEQUENCE: 116

Ile Glu Gln Cys Asp Tyr Pro Pro Leu Pro Ser Asp His Tyr Ser Glu
1               5                   10                  15

Glu Leu Arg
```

```
<210> SEQ ID NO 117
<211> LENGTH: 18
<212> TYPE: PRT
<213> ORGANISM: Homo Sapiens

<400> SEQUENCE: 117

Thr Thr Ala Ala His Ser Leu Val Gly Thr Pro Tyr Tyr Met Ser Pro
1               5                   10                  15
Glu Arg

<210> SEQ ID NO 118
<211> LENGTH: 10
<212> TYPE: PRT
<213> ORGANISM: Homo Sapiens

<400> SEQUENCE: 118

Val Gln Ile Phe Asp Leu Met Asp Ala Lys
1               5                   10

<210> SEQ ID NO 119
<211> LENGTH: 20
<212> TYPE: PRT
<213> ORGANISM: Homo Sapiens

<400> SEQUENCE: 119

Leu Asn Ser Gln Asn Leu Tyr Cys Ile Asn Ala Asp Gly Ser Gln Leu
1               5                   10                  15
Pro Leu Phe Arg
            20

<210> SEQ ID NO 120
<211> LENGTH: 13
<212> TYPE: PRT
<213> ORGANISM: Homo Sapiens

<400> SEQUENCE: 120

Val Phe Leu Ala Glu Cys Tyr Asn Leu Ser Pro Thr Lys
1               5                   10

<210> SEQ ID NO 121
<211> LENGTH: 10
<212> TYPE: PRT
<213> ORGANISM: Homo Sapiens

<400> SEQUENCE: 121

Val Val Ser Leu Glu Glu Pro Glu Leu Arg
1               5                   10

<210> SEQ ID NO 122
<211> LENGTH: 12
<212> TYPE: PRT
<213> ORGANISM: Homo Sapiens

<400> SEQUENCE: 122

Trp Met Gln Leu Trp Gln Glu Gln Gly Glu Ala Lys
1               5                   10

<210> SEQ ID NO 123
<211> LENGTH: 13
<212> TYPE: PRT
<213> ORGANISM: Homo Sapiens

<400> SEQUENCE: 123

Glu Pro Pro Lys Pro Ser Asp Ala Cys Gly Leu Ile Arg
```

```
1               5                  10
```

<210> SEQ ID NO 124
<211> LENGTH: 10
<212> TYPE: PRT
<213> ORGANISM: Homo Sapiens

<400> SEQUENCE: 124

```
Ile Val Ile Val Met Glu Tyr Ala Ser Arg
1               5                  10
```

<210> SEQ ID NO 125
<211> LENGTH: 13
<212> TYPE: PRT
<213> ORGANISM: Homo Sapiens

<400> SEQUENCE: 125

```
Leu Glu Asn Ile Leu Leu Asp Ala Asn Gly Asn Ile Lys
1               5                  10
```

<210> SEQ ID NO 126
<211> LENGTH: 20
<212> TYPE: PRT
<213> ORGANISM: Homo Sapiens

<400> SEQUENCE: 126

```
Ser Gly Pro Thr Pro Ser Ala Ala Glu Leu Ala Arg Pro Leu Ala Glu
1               5                  10                 15

Gly Leu Ile Lys
            20
```

<210> SEQ ID NO 127
<211> LENGTH: 19
<212> TYPE: PRT
<213> ORGANISM: Homo Sapiens

<400> SEQUENCE: 127

```
Val Gly Glu Gln Glu Ala Pro His Gly Gly His Pro Gly Ser Asp
1               5                  10                 15

Ser Ala Arg
```

<210> SEQ ID NO 128
<211> LENGTH: 17
<212> TYPE: PRT
<213> ORGANISM: Homo Sapiens

<400> SEQUENCE: 128

```
Ala Ser Ser Ser Ser Pro Leu Asp Tyr Ser Phe Gln Phe Thr Pro Ser
1               5                  10                 15

Arg
```

<210> SEQ ID NO 129
<211> LENGTH: 13
<212> TYPE: PRT
<213> ORGANISM: Homo Sapiens

<400> SEQUENCE: 129

```
His Gly Glu Ala Tyr Tyr Ser Glu Val Lys Pro Leu Lys
1               5                  10
```

<210> SEQ ID NO 130
<211> LENGTH: 15
<212> TYPE: PRT
<213> ORGANISM: Homo Sapiens

```
<400> SEQUENCE: 130

Ile Gly Glu Gly Ser Thr Gly Ile Val Cys Ile Ala Thr Glu Lys
1               5                   10                  15

<210> SEQ ID NO 131
<211> LENGTH: 15
<212> TYPE: PRT
<213> ORGANISM: Homo Sapiens

<400> SEQUENCE: 131

Ala Ala Pro Leu Ala Gly Phe Gly Tyr Gly Leu Pro Ile Ser Arg
1               5                   10                  15

<210> SEQ ID NO 132
<211> LENGTH: 16
<212> TYPE: PRT
<213> ORGANISM: Homo Sapiens

<400> SEQUENCE: 132

Leu Tyr Ser Met Glu Gly Val Gly Thr Asp Ala Val Ile Tyr Leu Lys
1               5                   10                  15

<210> SEQ ID NO 133
<211> LENGTH: 16
<212> TYPE: PRT
<213> ORGANISM: Homo Sapiens

<400> SEQUENCE: 133

Thr Thr Pro Glu Ala Asp Asp Trp Ser Asn Pro Ser Ser Glu Pro Arg
1               5                   10                  15

<210> SEQ ID NO 134
<211> LENGTH: 15
<212> TYPE: PRT
<213> ORGANISM: Homo Sapiens

<400> SEQUENCE: 134

Leu Pro Asn Tyr Asn Pro Glu Trp Phe Pro Leu Pro Thr Pro Arg
1               5                   10                  15

<210> SEQ ID NO 135
<211> LENGTH: 15
<212> TYPE: PRT
<213> ORGANISM: Homo Sapiens

<400> SEQUENCE: 135

Ser Leu Pro Phe Gly Ala Ala Ser Ser Tyr Leu Asn Leu Glu Lys
1               5                   10                  15

<210> SEQ ID NO 136
<211> LENGTH: 12
<212> TYPE: PRT
<213> ORGANISM: Homo Sapiens

<400> SEQUENCE: 136

Ser Asn Ser Asp Cys Phe Gln Glu Glu Asp Leu Arg
1               5                   10

<210> SEQ ID NO 137
<211> LENGTH: 16
<212> TYPE: PRT
<213> ORGANISM: Homo Sapiens

<400> SEQUENCE: 137
```

-continued

Val Ile Ser Met Asn Ala Glu Glu Gly Val Pro Phe Thr Ala Ile Arg
1               5                   10                  15

<210> SEQ ID NO 138
<211> LENGTH: 12
<212> TYPE: PRT
<213> ORGANISM: Homo Sapiens

<400> SEQUENCE: 138

Gly Gly Pro Ile Tyr Ile Ile Thr Glu Tyr Cys Arg
1               5                   10

<210> SEQ ID NO 139
<211> LENGTH: 13
<212> TYPE: PRT
<213> ORGANISM: Homo Sapiens

<400> SEQUENCE: 139

Gly Met Pro Gln Pro Asn Ile Ile Trp Ser Ala Cys Arg
1               5                   10

<210> SEQ ID NO 140
<211> LENGTH: 20
<212> TYPE: PRT
<213> ORGANISM: Homo Sapiens

<400> SEQUENCE: 140

Ile Met Ser His Leu Gly Pro His Leu Asn Val Val Asn Leu Leu Gly
1               5                   10                  15

Ala Cys Thr Lys
            20

<210> SEQ ID NO 141
<211> LENGTH: 11
<212> TYPE: PRT
<213> ORGANISM: Homo Sapiens

<400> SEQUENCE: 141

Ala Ala Pro Cys Asn Asp Leu His Ala Thr Lys
1               5                   10

<210> SEQ ID NO 142
<211> LENGTH: 9
<212> TYPE: PRT
<213> ORGANISM: Homo Sapiens

<400> SEQUENCE: 142

Gly Ala Leu Gln Glu Glu Leu Ala Arg
1               5

<210> SEQ ID NO 143
<211> LENGTH: 10
<212> TYPE: PRT
<213> ORGANISM: Homo Sapiens

<400> SEQUENCE: 143

Val Ser Asp Asn Leu Pro Val Ala Ile Lys
1               5                   10

<210> SEQ ID NO 144
<211> LENGTH: 12
<212> TYPE: PRT
<213> ORGANISM: Homo Sapiens

<400> SEQUENCE: 144

```
His Asp Phe Phe Leu Gln Gly Phe Thr Pro Asp Arg
1               5                   10
```

```
<210> SEQ ID NO 145
<211> LENGTH: 13
<212> TYPE: PRT
<213> ORGANISM: Homo Sapiens

<400> SEQUENCE: 145

Leu Gly Asn Phe Phe Ile Asn Glu Ala Met Glu Leu Lys
1               5                   10
```

```
<210> SEQ ID NO 146
<211> LENGTH: 14
<212> TYPE: PRT
<213> ORGANISM: Homo Sapiens

<400> SEQUENCE: 146

Thr Asp Glu Glu Leu Gln Pro Pro Thr Thr Val Ala Arg
1               5                   10
```

```
<210> SEQ ID NO 147
<211> LENGTH: 16
<212> TYPE: PRT
<213> ORGANISM: Homo Sapiens

<400> SEQUENCE: 147

Thr Ile Cys Gly Thr Pro Asn Tyr Leu Ser Pro Glu Val Leu Asn Lys
1               5                   10                  15
```

```
<210> SEQ ID NO 148
<211> LENGTH: 12
<212> TYPE: PRT
<213> ORGANISM: Homo Sapiens

<400> SEQUENCE: 148

Glu Val Val Ser Ser Thr Gly Val Leu Phe Val Lys
1               5                   10
```

```
<210> SEQ ID NO 149
<211> LENGTH: 11
<212> TYPE: PRT
<213> ORGANISM: Homo Sapiens

<400> SEQUENCE: 149

Asn Ile Leu Ile Gly Glu Gln Leu His Val Lys
1               5                   10
```

```
<210> SEQ ID NO 150
<211> LENGTH: 10
<212> TYPE: PRT
<213> ORGANISM: Homo Sapiens

<400> SEQUENCE: 150

Val Ser Gly Asn Pro Pro Thr Ile Arg
1               5                   10
```

```
<210> SEQ ID NO 151
<211> LENGTH: 9
<212> TYPE: PRT
<213> ORGANISM: Homo Sapiens

<400> SEQUENCE: 151

Met Glu Asn Ile Leu Leu Asp Glu Arg
1               5
```

```
<210> SEQ ID NO 152
<211> LENGTH: 13
<212> TYPE: PRT
<213> ORGANISM: Homo Sapiens

<400> SEQUENCE: 152

Cys Ala Gly Pro Ser Asn Ser Met Gln Leu Ala Ser Arg
1               5                   10

<210> SEQ ID NO 153
<211> LENGTH: 11
<212> TYPE: PRT
<213> ORGANISM: Homo Sapiens

<400> SEQUENCE: 153

Asp Ala Ile Val Glu Ala Leu Glu Thr Asn Arg
1               5                   10

<210> SEQ ID NO 154
<211> LENGTH: 14
<212> TYPE: PRT
<213> ORGANISM: Homo Sapiens

<400> SEQUENCE: 154

Leu Asp Thr Leu Ala Thr Gly His Leu Phe Gln Glu Val Arg
1               5                   10

<210> SEQ ID NO 155
<211> LENGTH: 19
<212> TYPE: PRT
<213> ORGANISM: Homo Sapiens

<400> SEQUENCE: 155

Met Cys Ile Ser Ser Thr Gly Asn Ala Gly Gln Val Pro Ala Val Gly
1               5                   10                  15

Gly Ile Lys

<210> SEQ ID NO 156
<211> LENGTH: 20
<212> TYPE: PRT
<213> ORGANISM: Homo Sapiens

<400> SEQUENCE: 156

Lys Pro Pro Val Phe Asp Glu Asn Glu Asp Val Asn Phe Asp His Phe
1               5                   10                  15

Glu Ile Leu Arg
            20

<210> SEQ ID NO 157
<211> LENGTH: 9
<212> TYPE: PRT
<213> ORGANISM: Homo Sapiens

<400> SEQUENCE: 157

Leu Leu Glu Pro Asn Pro Asp Gln Arg
1               5

<210> SEQ ID NO 158
<211> LENGTH: 16
<212> TYPE: PRT
<213> ORGANISM: Homo Sapiens

<400> SEQUENCE: 158

Leu Gln Asp Gly Cys Asn Asn Asn Leu Leu Thr His Thr Cys Thr Arg
```

```
                 1               5                  10                 15
```

<210> SEQ ID NO 159
<211> LENGTH: 15
<212> TYPE: PRT
<213> ORGANISM: Homo Sapiens

<400> SEQUENCE: 159

```
Leu Tyr Ile Cys Glu Leu Ala Leu Ala Leu Glu Tyr Leu Gln Arg
1               5                  10                 15
```

<210> SEQ ID NO 160
<211> LENGTH: 15
<212> TYPE: PRT
<213> ORGANISM: Homo Sapiens

<400> SEQUENCE: 160

```
Ala Val Cys Met Asn Gly Thr Glu Ala Ala Gln Leu Ser Thr Lys
1               5                  10                 15
```

<210> SEQ ID NO 161
<211> LENGTH: 16
<212> TYPE: PRT
<213> ORGANISM: Homo Sapiens

<400> SEQUENCE: 161

```
Asp Ile Lys Pro Gly Asn Leu Leu Leu Thr Thr Gly Gly Thr Leu Lys
1               5                  10                 15
```

<210> SEQ ID NO 162
<211> LENGTH: 20
<212> TYPE: PRT
<213> ORGANISM: Homo Sapiens

<400> SEQUENCE: 162

```
Ile Ser Asp Leu Gly Val Ala Glu Ala Leu His Pro Phe Ala Ala Asp
1               5                  10                 15

Asp Thr Cys Arg
            20
```

<210> SEQ ID NO 163
<211> LENGTH: 14
<212> TYPE: PRT
<213> ORGANISM: Homo Sapiens

<400> SEQUENCE: 163

```
Asn Val Ile Gln Leu Val Asp Val Leu Tyr Asn Glu Glu Lys
1               5                  10
```

<210> SEQ ID NO 164
<211> LENGTH: 14
<212> TYPE: PRT
<213> ORGANISM: Homo Sapiens

<400> SEQUENCE: 164

```
Tyr Leu Met Gly Asp Leu Leu Gly Glu Gly Ser Tyr Gly Lys
1               5                  10
```

<210> SEQ ID NO 165
<211> LENGTH: 13
<212> TYPE: PRT
<213> ORGANISM: Homo Sapiens

<400> SEQUENCE: 165

```
Ala Cys Asp Gly Arg Pro Tyr Ala Gly Ala Val Gln Lys
```

<210> SEQ ID NO 166
<211> LENGTH: 14
<212> TYPE: PRT
<213> ORGANISM: Homo Sapiens

<400> SEQUENCE: 166

Asp Ala Gly Ser Trp Trp Leu Ala Val Pro Gly Ala Gly Arg
1               5                   10

<210> SEQ ID NO 167
<211> LENGTH: 13
<212> TYPE: PRT
<213> ORGANISM: Homo Sapiens

<400> SEQUENCE: 167

Gly Leu Phe Glu Asp Ala Leu Pro Pro Ile Val Leu Arg
1               5                   10

<210> SEQ ID NO 168
<211> LENGTH: 15
<212> TYPE: PRT
<213> ORGANISM: Homo Sapiens

<400> SEQUENCE: 168

Asp Ser Ser Gln Pro Gly Leu Tyr Thr Val Ser Leu Tyr Thr Lys
1               5                   10                  15

<210> SEQ ID NO 169
<211> LENGTH: 11
<212> TYPE: PRT
<213> ORGANISM: Homo Sapiens

<400> SEQUENCE: 169

Asn Asp Asp Gly Val Ile Pro Cys Gln Asn Lys
1               5                   10

<210> SEQ ID NO 170
<211> LENGTH: 9
<212> TYPE: PRT
<213> ORGANISM: Homo Sapiens

<400> SEQUENCE: 170

Asp Tyr Glu Pro Pro Phe Gly Ser Lys
1               5

<210> SEQ ID NO 171
<211> LENGTH: 15
<212> TYPE: PRT
<213> ORGANISM: Homo Sapiens

<400> SEQUENCE: 171

Leu Pro Tyr His Asp Phe Ile Leu Glu Asp Ala Ala Ser Pro Lys
1               5                   10                  15

<210> SEQ ID NO 172
<211> LENGTH: 15
<212> TYPE: PRT
<213> ORGANISM: Homo Sapiens

<400> SEQUENCE: 172

Asn Asp Leu Thr Cys Cys Leu Cys Asp Phe Gly Leu Ser Leu Arg
1               5                   10                  15

```
<210> SEQ ID NO 173
<211> LENGTH: 16
<212> TYPE: PRT
<213> ORGANISM: Homo Sapiens

<400> SEQUENCE: 173

Ser Val Asn Asn Asp Met Ile Val Thr Asp Asn Asn Gly Ala Val Lys
1               5                   10                  15

<210> SEQ ID NO 174
<211> LENGTH: 10
<212> TYPE: PRT
<213> ORGANISM: Homo Sapiens

<400> SEQUENCE: 174

Tyr Met Ala Pro Glu Val Leu Glu Ser Arg
1               5                   10

<210> SEQ ID NO 175
<211> LENGTH: 22
<212> TYPE: PRT
<213> ORGANISM: Homo Sapiens

<400> SEQUENCE: 175

Leu Ile Phe Gln Asn Cys Ala Glu Phe Asn Glu Pro Asp Ser Glu Val
1               5                   10                  15

Ala Asn Ala Gly Ile Lys
            20

<210> SEQ ID NO 176
<211> LENGTH: 13
<212> TYPE: PRT
<213> ORGANISM: Homo Sapiens

<400> SEQUENCE: 176

Leu Met Gln Gln Gln Gln Glu Val Ala Gly Leu Ser Lys
1               5                   10

<210> SEQ ID NO 177
<211> LENGTH: 22
<212> TYPE: PRT
<213> ORGANISM: Homo Sapiens

<400> SEQUENCE: 177

Ser Asp Ala Pro Asp Ser Thr Gly Asp Gln Pro Gly Leu His Gln Asp
1               5                   10                  15

Asn Ser Ser Asn Gly Lys
            20

<210> SEQ ID NO 178
<211> LENGTH: 13
<212> TYPE: PRT
<213> ORGANISM: Homo Sapiens

<400> SEQUENCE: 178

Leu Leu Gln Gln Gln Asn Asp Ile Thr Gly Leu Ser Arg
1               5                   10

<210> SEQ ID NO 179
<211> LENGTH: 11
<212> TYPE: PRT
<213> ORGANISM: Homo Sapiens

<400> SEQUENCE: 179

Thr Glu Pro Ala Asp Met Asn Glu Ser Cys Lys
```

```
1               5                   10
```

<210> SEQ ID NO 180
<211> LENGTH: 13
<212> TYPE: PRT
<213> ORGANISM: Homo Sapiens

<400> SEQUENCE: 180

```
Ala Ala Val Tyr His His Phe Ile Ser Asp Gly Val Arg
1               5                   10
```

<210> SEQ ID NO 181
<211> LENGTH: 13
<212> TYPE: PRT
<213> ORGANISM: Homo Sapiens

<400> SEQUENCE: 181

```
His Ile Gln Asn Ile Asp Ile Gln His Leu Ala Gly Lys
1               5                   10
```

<210> SEQ ID NO 182
<211> LENGTH: 13
<212> TYPE: PRT
<213> ORGANISM: Homo Sapiens

<400> SEQUENCE: 182

```
Gly Gly Gln Glu His Phe Ala His Leu Leu Ile Leu Arg
1               5                   10
```

<210> SEQ ID NO 183
<211> LENGTH: 14
<212> TYPE: PRT
<213> ORGANISM: Homo Sapiens

<400> SEQUENCE: 183

```
Thr Glu Val Ser Ser Asn His Val Leu Ile Tyr Leu Asp Lys
1               5                   10
```

<210> SEQ ID NO 184
<211> LENGTH: 14
<212> TYPE: PRT
<213> ORGANISM: Homo Sapiens

<400> SEQUENCE: 184

```
Thr Glu His Pro Phe Thr Val Glu Glu Phe Val Leu Pro Lys
1               5                   10
```

<210> SEQ ID NO 185
<211> LENGTH: 13
<212> TYPE: PRT
<213> ORGANISM: Homo Sapiens

<400> SEQUENCE: 185

```
Asn Gln Gly Asn Thr Trp Leu Thr Ala Phe Val Leu Lys
1               5                   10
```

<210> SEQ ID NO 186
<211> LENGTH: 14
<212> TYPE: PRT
<213> ORGANISM: Homo Sapiens

<400> SEQUENCE: 186

```
Leu Val Ala Tyr Tyr Thr Leu Ile Gly Ala Ser Gly Gln Arg
1               5                   10
```

```
<210> SEQ ID NO 187
<211> LENGTH: 14
<212> TYPE: PRT
<213> ORGANISM: Homo Sapiens

<400> SEQUENCE: 187

Thr Thr Asn Ile Gln Gly Ile Asn Leu Leu Phe Ser Ser Arg
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Synthetic oligopeptide

<400> SEQUENCE: 188

His Gln Asp Gln Thr Leu Arg
1               5

<210> SEQ ID NO 189
<211> LENGTH: 10
<212> TYPE: PRT
<213> ORGANISM: Artificial Sequence
<220> FEATURE:
<223> OTHER INFORMATION: Synthetic oligopeptide

<400> SEQUENCE: 189

Leu Glu Leu Asn Gly Asn Asp Ile Thr Arg
1               5                   10
```